United States Patent
Knuebel et al.

(10) Patent No.: US 10,420,717 B2
(45) Date of Patent: Sep. 24, 2019

(54) BUNTE SALTS FROM AMINO ACIDS AND OLIGOPEPTIDES AS PROTECTIVE INGREDIENTS IN HAIR TREATMENT MEANS

(71) Applicant: Henkel AG & Co. KGaA, Duesseldorf (DE)

(72) Inventors: Georg Knuebel, Duesseldorf (DE); Thomas Foerster, Duesseldorf (DE); Erik Schulze zur Wiesche, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/752,462

(22) PCT Filed: Aug. 2, 2016

(86) PCT No.: PCT/EP2016/068362
§ 371 (c)(1),
(2) Date: Feb. 13, 2018

(87) PCT Pub. No.: WO2017/029107
PCT Pub. Date: Feb. 23, 2017

(65) Prior Publication Data
US 2019/0008740 A1   Jan. 10, 2019

(30) Foreign Application Priority Data

Aug. 14, 2015 (DE) .................. 10 2015 215 580
Nov. 11, 2015 (DE) .................. 10 2015 222 147

(51) Int. Cl.
| | | |
|---|---|---|
| *A61K 8/46* | (2006.01) | |
| *A61K 8/44* | (2006.01) | |
| *A61Q 5/10* | (2006.01) | |
| *A61K 8/22* | (2006.01) | |

(52) U.S. Cl.
CPC .................. *A61K 8/46* (2013.01); *A61K 8/22* (2013.01); *A61K 8/447* (2013.01); *A61Q 5/10* (2013.01); *A61K 2800/882* (2013.01); *A61K 2800/884* (2013.01)

(58) Field of Classification Search
CPC ........................................ A61K 8/46
See application file for complete search history.

(56) References Cited

FOREIGN PATENT DOCUMENTS

| DE | 10 2012 222 286.3 A1 | 9/2013 |
|---|---|---|
| GB | 2115427 A | 9/1983 |
| JP | 2006273782 A | 10/2006 |

OTHER PUBLICATIONS

Tanabe et al., machine translation (Google) of JP 2006/273782 A (Oct. 12, 2006).*
Wolfram et al., TGA Cosmetic Journal (1970), 2(1), pp. 45-51.*
EPO, International Search Report and Written Opinion issued in International Application No. PCT/EP2016/068362, dated Sep. 27, 2016.
Brian Milligan and J.M. Swan., Bunte Salts (RSSO3Na), Rev. Pure Appl. Chem, vol. 12, p. 72-94, (1962).

* cited by examiner

*Primary Examiner* — Brian J Davis
(74) *Attorney, Agent, or Firm* — Lorenz & Kopf, LLP

(57) ABSTRACT

A hair treatment agent is provided herein. The hair treatment agent includes in a cosmetic carrier (a) at least one compound of the general formula (I). $R_1$ denotes a hydrogen atom or a structural element of formula (II). x denotes an integer from 1 to 100. The radical $R_2$ in each of the structural elements of formula (II) can be selected independently of the preceding structural element of formula (II). M1 denotes the grouping —OM2 or a structural element of formula (III). y denotes an integer from 1 to 100. M2 denotes a hydrogen atom, an equivalent of one or more cations or an ammonia ion $(NH_4)^+$.

18 Claims, No Drawings

BUNTE SALTS FROM AMINO ACIDS AND OLIGOPEPTIDES AS PROTECTIVE INGREDIENTS IN HAIR TREATMENT MEANS

This application is a U.S. National-Stage entry under 35 U.S.C. § 371 based on International Application No. PCT/EP2016/068362, filed Aug. 2, 2016 which was published under PCT Article 21(2) and which claims priority to German Application No. 10 2015 215 580.3, filed Aug. 14, 2015, and German Application No. 10 2015 222 147.4, filed Nov. 11, 2015, which are all hereby incorporated in their entirety by reference.

TECHNICAL FIELD

The present disclosure relates to hair treatment agents containing functional groups of amino acids and special oligopeptides or peptides. These hair treatment agents are particularly suitable for gentle bleaching or lightening dyes of hair. A further subject of the present disclosure is a kit containing two separately packaged preparations. The first preparation is the aforementioned hair treatment agent and the second preparation is an oxidant preparation containing at least one oxidant. A third subject of the present disclosure is a method for oxidative dyeing and/or lightening of hair in which the preparations of the kit are applied to the keratinous fibers—either in succession or as a mixture—and washed out of the hair.

BACKGROUND

The change in hair color is an important area of modern cosmetics and enables an adaptation of the hair's appearance to current fashion trends and the individual wishes of the individual person. The bleaching of some hair color, however, has always been the wish of many consumers, because a blond hair color is considered attractive and desirable from a fashion perspective. For this purpose, various bleaching agents in the market are available with varying bleaching performance. The oxidants contained in these products are capable of lightening the hair fibers by means of oxidative destruction of the hair's own color, melanin. For a moderate bleaching effect, use of hydrogen peroxide is suitable—optionally with the use of ammonia or other alkalizing agents—as a sole oxidizing agent; for a stronger bleaching effect, a mixture of hydrogen peroxide and peroxodisulfate salts and/or peroxomonosulfate salts is normally used.

However, the bleaching usually also entails damage to the hair, because, in addition to the color of the hair, the remaining structural components are also oxidatively damaged. Depending on the character of the degree of damage, this can vary from rough, brittle and difficult-to-comb hair to a reduce resilience and strength of the hair to hair break. The greater the amount of hydrogen peroxide that is used, and optionally peroxodisulfate, the greater the damage caused to the keratinous fibers normally is.

To avoid or minimize the hair damage cause by the oxidative processes, manufacturers are constantly looking for new ingredients and active ingredients.

Appropriate active ingredients can be used as pre-treatment agents before the oxidative dyeing and/or lightening process, during the oxidative treatment—as a supplement to the oxidative color or bleaching agent—or as a post-treatment agent. Of particular interest is the presence of active ingredients that can be used as a pre-treatment agent and as a post-treatment agent, which can also be added to the oxidative bleaching or dyeing agent and thus minimize or prevent damage during the oxidative hair treatment process.

Therefore, the problem addressed by the present disclosure is to prepare novel agents for the treatment of hair, which minimize or prevent the hair damage caused by an oxidative hair treatment process. These agents should be suitable for universal use, i.e. they should be suitable for use as a pre-treatment and/or post-treatment agent and also added directly to the oxidative bleaching or dyeing agent. Since the agents should also be used as an additive to an already existing bleaching and/or dyeing product, the present disclosure of active ingredients that already have a good effect in low amounts is of particular interest.

Various substances that can be ascribed a nurturing effect are already known from the prior art. They are normally absorbed on the hair surface and smooth the roughened and/or damaged cuticula. A reduction of hair damage can also be achieved with these compounds. However, if the consumer washes their hair, these substances are rinsed off of the surface of the hair again. For this reason, achievement of a long-term nurturing effect is not possible with the use of substances that only perform the nurturing effect on the cuticula with application on the surface.

The present application also addressed the problem of preparing hair treatment agents that have a long-term nurturing effect and the nurturing effect is also retained after repeatedly washing the hair.

BRIEF SUMMARY

A hair treatment agent is provided herein. The hair treatment agent includes in a cosmetic carrier (a) at least one compound of the general formula (I). $R_1$ denotes a hydrogen atom or a structural element of formula (II). x denotes an integer from 1 to 100. The radical $R_2$ in each of the structural elements of formula (II) can be selected independently of the preceding structural element of formula (II). $R_2$ denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group. M1 denotes the grouping —OM2 or a structural element of formula (III). y denotes an integer from 1 to 100. The radical $R_3$ in each of the structural elements of formula (III) can be selected independently of the preceding structural element of formula (III). $R_3$ denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl) methyl group. M2 denotes a hydrogen atom, an equivalent of one or more cations or an ammonia ion $(NH_4)^+$.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, it has now been demonstrated that the use of functional groups of special amino acids, oligopeptides and peptides in hair treatment agents achieves an especially long-lasting nurturing effect. Hair treatment agents that contain these functional groups could be used as a pre-treatment agent as well as a post-treatment agent. It was particularly surprising that the agents also demonstrated a strong effect with the use of oxidative bleaching and/or dyeing agents—even if these bleaching products containing oxidatively very aggressive persulfates were added.

A first object of this present disclosure is therefore a hair treatment agent containing, in a cosmetic carrier,
(a) at least one compound of the general formula (I)

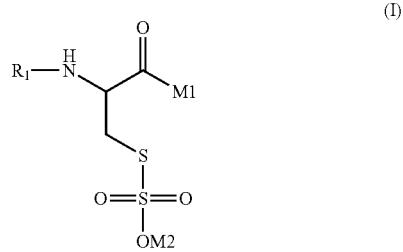

(I)

wherein
R1 denotes a hydrogen atom or a structural element of formula (II)

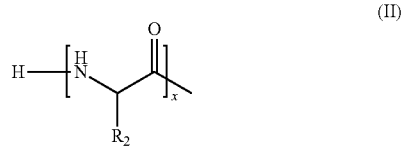

(II)

wherein
x denotes an integer from 1 to 100,
the radical R2 in each of the structural elements of formula (II) can be selected independently of the preceding structural element of formula (II),
R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M1 denotes the grouping —OM2 or a structural element of formula (III)

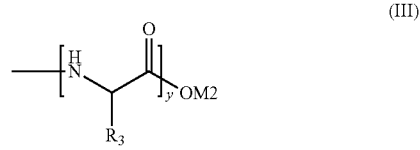

(III)

wherein
y denotes an integer from 1 to 100,
the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 denotes a hydrogen atom, an equivalent of one or more cations or an ammonia ion $(NH_4)^+$.

The term hair treatment agent is understood to mean an agent for treating human hair, examples of which include shampoo, conditioner, care drops, hair coloring agent, bleaching agent, gel or a care cream.

The agents as contemplated herein contain the essential compound of formula (I) in a cosmetic carrier, preferably a suitable hydrous or hydrous-alcohol carrier. Carriers such as creams, emulsions, gels or surfactant-containing, foaming solutions, such as shampoos, foaming aerosols, foam formulations or other preparations suitable for application on the hair, are used for treatment of the hair. However, it is also conceivable that the agents could be integrated in a powdery or a tablet-like formulation.

To the extent required by this present disclosure, anhydrous-alcoholic solutions are anhydrous solutions containing from about 0.1 to about 70 wt. % $C_1$-$C_4$ alcohol, more particularly ethanol and/or isopropanol. The agents as contemplated herein can also contain other organic solvents, such as methoxybutanol, benzyl alcohol, ethyldiglycol or 1,2-propylene glycol. All water-soluble organic solvents are preferred. According to this present disclosure, the aqueous carrier contains at least 30 wt. % of water, in particular, at least about 50 wt. % water, based on the total weight of the agent. Preference is given to aqueous carriers as contemplated herein.

The essential ingredient (a) of formula as contemplated herein is the functional group of an amino acid, an oligopeptide or a peptide, which is represented by the compound of formula (I)

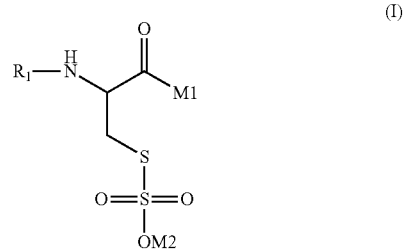

(I)

wherein
R1 denotes a hydrogen atom or a structural element of formula (II)

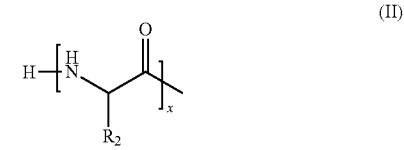

(II)

wherein
x denotes an integer from 1 to 100,
the radical R2 in each of the structural elements of formula (II) can be selected independently of the preceding structural element of formula (II), R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

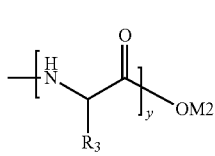

(III)

wherein
y denotes an integer from 1 to 100,
the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

The radical R1 can denote a hydrogen atom or a structural element of formula (II)

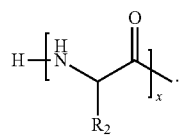

(II)

The structural element of formula (II) is also exemplified by the repetition index x, where x denotes an integer from 1 to 100. The repetition index x indicates how many structural elements of formula (II) are included in the compound of formula (I).

Preferably, x denotes an integer from 1 to 50, more preferably an integer from 1 to 20, particularly preferably from 1 to 10.

If x denotes the integer 10, for example, the compound of formula (I) contains 10 structural elements of formula (II).

In the process, it is essential that the radical R2 in each of the structural elements of formula (II) can be selected independently of the preceding structural element of formula (II). If the compounds of formula (I) contain, for example, 10 structural units of formula (II), these 10 structural units can be equal or different.

The radical R2 denotes a hydrogen atom, a methyl group, an isopropyl group, a 2-methylpropyl group, a 1-methylpropyl group, a benzyl group, a 4-hydroxybenzyl group, a hydroxy methyl group, a 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl) methyl group, If x denotes the integer 1, the compound of formula (I) contains one structural element of formula (II). In this connection, the linking of structural elements takes place as represented in formula (I-a).

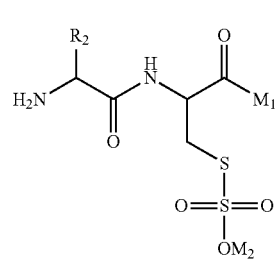

(I-a)

If x denotes the integer 2, the compound of formula (I) contains two structural elements of formula (II). In this connection, the linking of structural elements takes place as represented in formula (I-b).

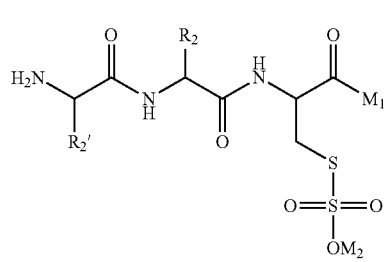

(I-b)

In the process, any of the R2 radicals can be selected independently of the other R2 radical. The R2 radicals which can be selected independently of each other are identified in formula (I-b) as R2 and R2'.

If x denotes the integer 3, the compound of formula (I) contains three structural elements of formula (III). In this connection, the linking of structural elements takes place as represented in formula (I-c).

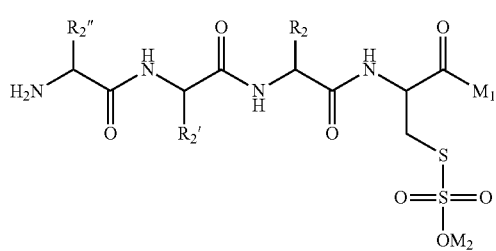

(I-c)

In the process, any of the R2 radicals can be selected independently of the other R2 radical. The R2 radicals which can be selected independently of each other are identified in formula (I-c) as R2, R2' and R2".

If x denotes the integer 4, the compound of formula (I) contains four structural elements of formula (II). In this connection, the linking of structural elements takes place as represented in formula (I-d).

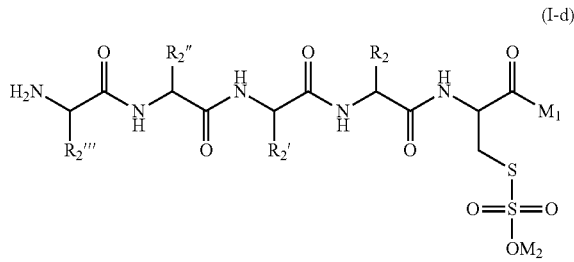

(I-d)

In the process, any of the R2 radicals can be selected independently of the other R2 radicals. The R2 radicals which can be selected independently of each other are identified in formula (I-d) as R2, R2' and R2" and R'".

If x denotes the integer 5, the compound of formula (I) contains five structural elements of formula (II). In this connection, the linking of structural elements takes place as represented in formula (I-e).

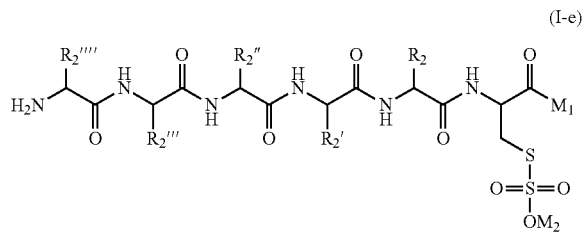

(I-e)

In the process, any of the R2 radicals can be selected independently of the other R2 radicals. The R2 radicals which can be selected independently of each other are identified in formula (I-e) as R2, R2' and R2", R'" and R''".

If x denotes the integer 6, the compound of formula (I) contains six structural elements of formula (II). In this connection, the linking of structural elements takes place as represented in formula (I-f).

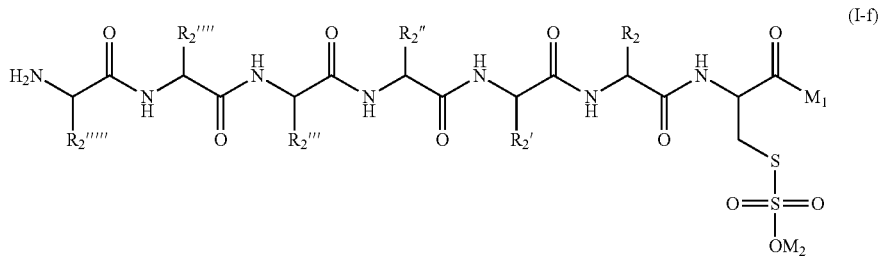

(I-f)

In the process, any of the R2 radicals can be selected independently of the other R2 radicals. The R2 radicals which can be selected independently of each other are identified in formula (I-f) as R2, R2' and R2", R'", R''" and R'''''.

The linking of all additional x structural elements takes place analogously.

Therefore, the structural element of formula (II) is an amino acid that is peptidically linked via its amino and/or acidic function within the compound of formula (I). If the amino acid is a cysteine, it can also be in the form of a functional group.

If the radical R2 denotes a hydrogen atom, the structural element of formula (II) is based on the amino acid glycine. If the radical R2 denotes a methyl group, the structural element of formula (II) is based on the amino acid alanine.

If the radical R2 denotes an isopropyl group (i.e. a group $(H_3C)_2CH—$), the structural element of formula (II) is based on the amino acid valine.

If the radical R2 denotes a 2-methylpropyl group (i.e. a group $(H_3C)_2CH—CH_2—$), the structural element of formula (II) is based on the amino acid leucine.

If the radical R2 denotes a 1-methylpropyl group (i.e. a group H3C—CH2-CH(CH3)-), the structural element of formula (II) is based on the amino acid isoleucine.

If the radical R2 denotes a benzyl group (i.e. a group $C_6H_5—CH_2—$), the structural element of formula (II) is based on the amino acid phenylalanine.

If the radical R2 denotes a 4-hydroxybenzyl group (i.e. a group $4-OH—C_6H_5—CH_2—$), the structural element of formula (II) is based on the amino acid tyrosine.

If the radical R2 denotes a hydroxymethyl group (i.e. a group HO—CH2-), the structural element of formula (II) is based on the amino acid serin.

If the radical R2 denotes a 1-hydroxyethyl group (i.e. a group H3C—CH(OH)—), the structural element of formula (II) is based on the amino acid threonine.

If the radical R2 denotes a 4-aminobutyl group (i.e. a group H2N—CH2-CH2-CH2-CH2-), the structural element of formula (II) is based on the amino acid lysine.

If the radical R2 denotes a 3-Carbamimidamidopropyl group (i.e. a group $H_2N—C(NH)—NH—CH_2—CH_2—CH_2—$), the structural element of formula (II) is based on the amino acid arginine.

If the radical R2 denotes a 2-carboxyethyl group (i.e. a group HOOC—CH2-CH2-), the structural element of formula (II) is based on the amino acid glutamic acid.

If the radical R2 denotes a carboxymethyl group (i.e. a group HOOC—CH2-), the structural element of formula (II) is based on the amino acid aspartic acid.

If the radical R2 denotes a 2-carbamoylethyl group (i.e. a group H2N—C(O)—CH2-CH2-), the structural element of formula (II) is based on the amino acid glutamine.

If the radical R2 denotes a carbamoylethyl group (i.e. a group H2N—C(O)—CH2-), the structural element of formula (II) is based on the amino acid Asparagine.

If the radical R2 denotes a sulfanylmethyl group (i.e. a group HS—CH2-), the structural element of formula (II) is based on the amino acid cysteine.

If the radical R2 denotes a 2-(methylsulfanyl)ethyl group (i.e. a group H3C—S—CH2-CH2-), the structural element of formula (II) is based on the amino acid methionine.

If the radical R2 denotes a 1H-imidazol-4-ylmethyl group, the structural element of formula (II) is based on the amino acid histidine.

If the radical R2 denotes a 1H-indol-3-ylmethyl group, the structural element of formula (II) is based on the amino acid tryptophan.

Finally, the radical R2 can also denote a (sulfosulfanyl)methyl group, in which case it is a functional group structure of formula HO—S(O$_2$)—S—CH$_2$—.

Depending on the pH value of the hair treatment agent, the functional group structure of formula HO—S(O$_2$)—S—CH$_2$— is also present in its deprotonated form.

A particularly preferred embodiment as contemplated herein is a hair treatment agent with a cosmetic carrier containing (a) at least one compound of the general formula (I-a)

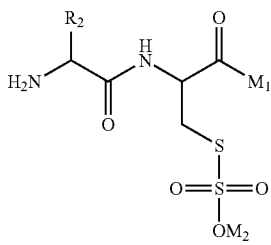
(Ia)

wherein

R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

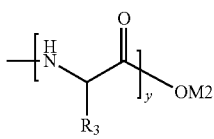
(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion (NH$_4$)$^+$.

A particularly preferred embodiment as contemplated herein is also a hair treatment agent with a cosmetic carrier containing (a) at least one compound of the general formula (I-b)

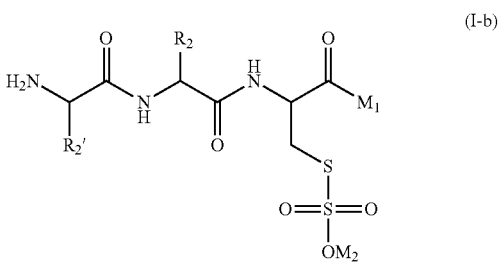
(I-b)

wherein

R2 and R2', independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

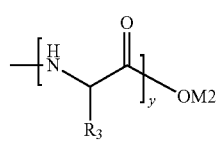
(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion (NH$_4$)$^+$.

A particularly preferred embodiment as contemplated herein is also a hair treatment agent with a cosmetic carrier containing (a) at least one compound of the general formula (I-c)

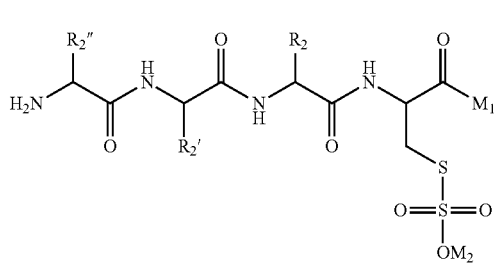

(I-c)

wherein

R2, R2' and R2", independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

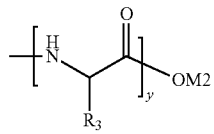

(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I-d)

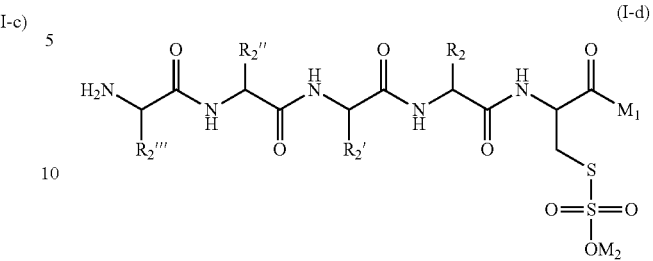

(I-d)

wherein

R2, R2', R2" and R2''', independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

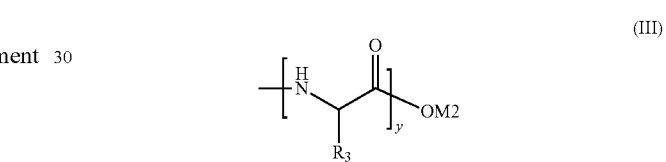

(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I-e)

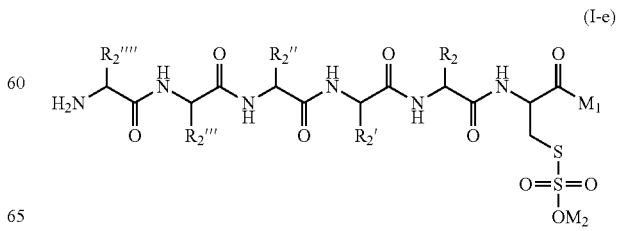

(I-e)

wherein

R2, R2', R2'', R''' and R'''', independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

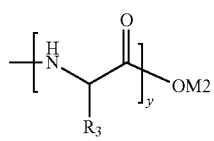

(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I-f)

M1 denotes the grouping —OM2 or a structural element of formula (III)

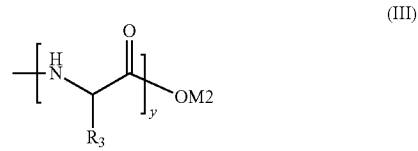

(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

Within the compound of formula (I), M1 denotes grouping —OM2 or a structural element of formula (III)

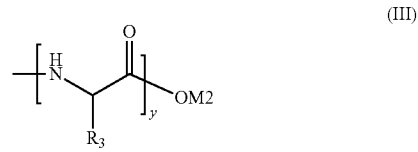

(III)

The structural element of formula (III) is—exactly like the structural element of formula (II)—exemplified by the repetition index y, where y denotes an integer from 1 to 100.

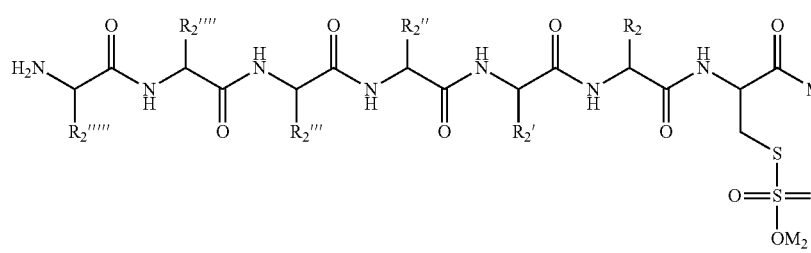

(I-f)

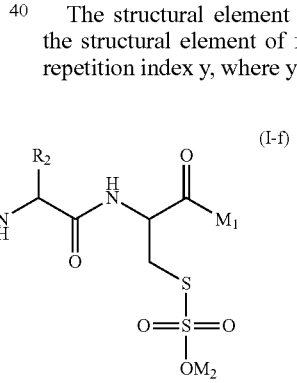

wherein

R2, R2', R2'', R2''', R2'''' and R2''''' independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, The repetition index y indicates how many structural elements of formula (III) are included in the compound of formula (I).

Preferably, y denotes an integer from 1 to 50, more preferably an integer from 1 to 20, particularly preferably from 1 to 10.

If y denotes the integer 10, for example, the compound of formula (I) contains 10 structural elements of formula (III).

In the process, it is essential that the radical R3 in each of the structural elements of formula (III) can be selected independently of the preceding structural element of formula (III). If the compounds of formula (I) contain, for example, 10 structural units of formula (III), these 10 structural units can be equal or different.

The radical R3 denotes a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group.

The structural element of formula (III) is also an amino acid which is petidically linked via its amino and/or acid function within the compound of formula (I). If the amino acid is a cysteine, it can also be in the form of a functional group.

If y denotes the integer 1, the compound of formula (I) contains one structural element of formula (III). In this connection, the linking of structural elements takes place as represented in formula (I-I).

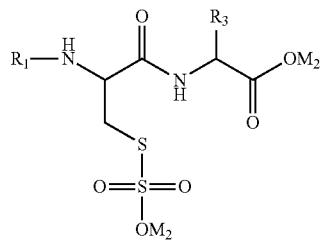

(I-I)

If y denotes the integer 2, the compound of formula (I) contains two structural elements of formula (III). In this connection, the linking of structural elements takes place as represented in formula (I-II).

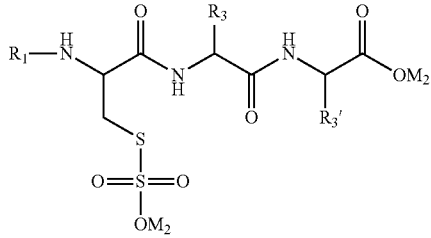

(I-II)

In the process, any of the R3 radicals can be selected independently of the other R3 radical. The R3 radicals which can be selected independently of each other are identified in formula (I-II) as R3 and R3'.

If y denotes the integer 3, the compound of formula (I) contains three structural elements of formula (III). In this connection, the linking of structural elements takes place as represented in formula (I-III).

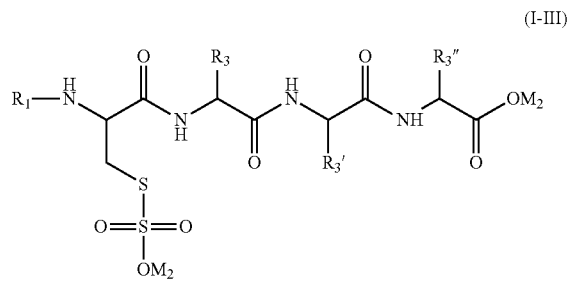

(I-III)

In the process, any of the R3 radicals can be selected independently of the other R3 radicals. The R3 radicals which can be selected independently of each other are identified in formula (I-III) as R3, R3' and R3".

If x denotes the integer 4, the compound of formula (I) contains four structural elements of formula (III). In this connection, the linking of structural elements takes place as represented in formula (I-IV).

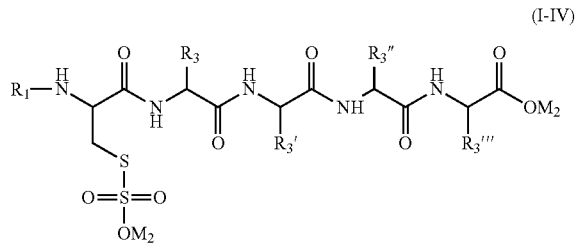

(I-IV)

In the process, any of the R3 radicals can be selected independently of the other R3 radicals. The R3 radicals which can be selected independently of each other are identified in formula (I-IV) as R3, R3', R3" and R'".

If y denotes the integer 5, the compound of formula (I) contains five structural elements of formula (II). In this connection, the linking of structural elements takes place as represented in formula (I-V).

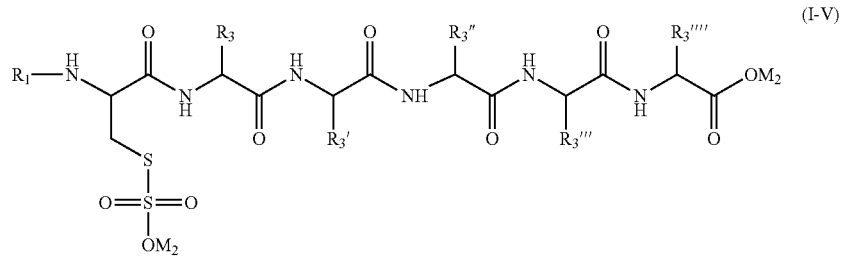

(I-V)

In the process, any of the R3 radicals can be selected independently of the other R3 radicals. The R3 radicals which can be selected independently of each other are identified in formula (I-e) as R3, R3', R3", R'" and R"".

If y denotes the integer 6, the compound of formula (I) contains six structural elements of formula (II). In this connection, the linking of structural elements takes place as represented in formula (I-VI).

oylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a

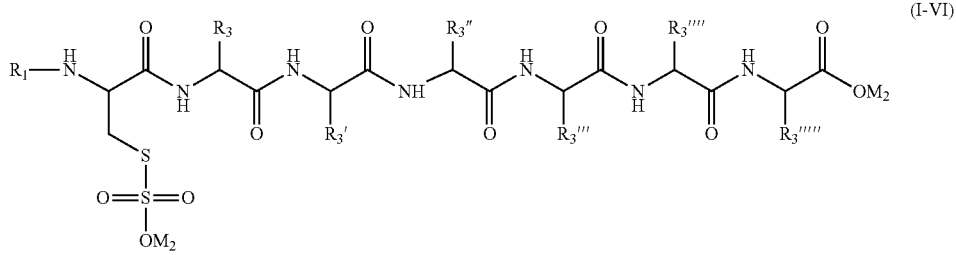

(I-VI)

In the process, any of the R3 radicals can be selected independently of the other R3 radicals. The R3 radicals which can be selected independently of each other are identified in formula (I-VI) as R3, R3', R3", R'", R"" and R3""".

A particularly preferred embodiment as contemplated herein is a hair treatment agent with a cosmetic carrier containing
(a) at least one compound of the general formula (I-I)

carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing
(a) at least one compound of the general formula (I-II)

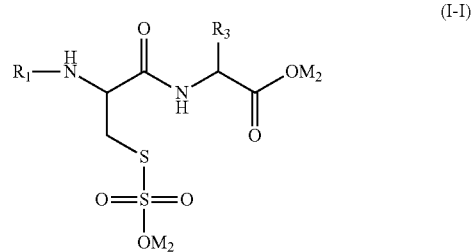

(I-I)

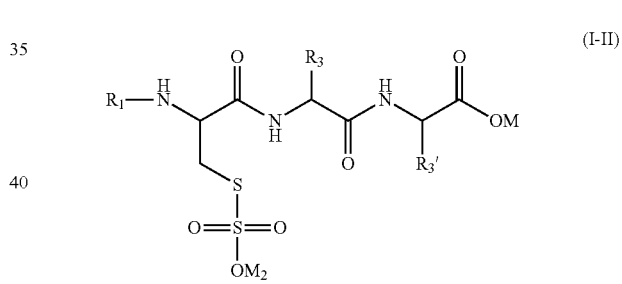

(I-II)

wherein
R1 denotes a hydrogen atom or a structural element of formula (II)

wherein
R1 denotes a hydrogen atom or a structural element of formula (II)

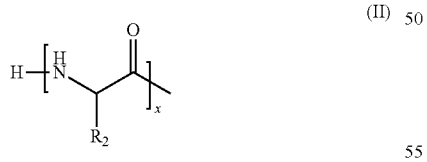

(II)

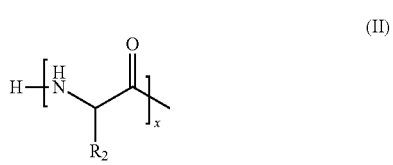

(II)

wherein
x denotes an integer from 1 to 10,
the radical R2 in each of the structural elements of formula (II) can be selected independently of the preceding structural element of formula (II),
R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamwherein
x denotes an integer from 1 to 10,
the radical R2 in each of the structural elements of formula (II) can be selected independently of the preceding structural element of formula (II),
R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, R3 and R3', independently of each other, denote a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$. A particularly preferred embodiment as contemplated herein is a hair treatment agent with a cosmetic carrier containing (a) at least one compound of the general formula (I-III)

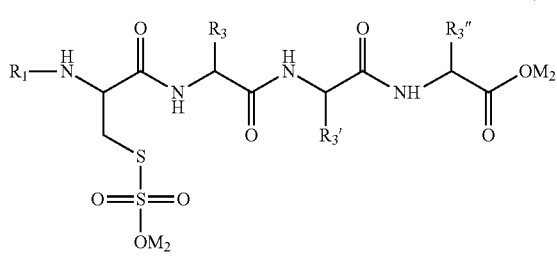

(I-III)

wherein
R1 denotes a hydrogen atom or a structural element of formula (II)

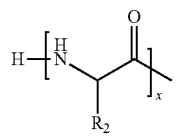

(II)

wherein
x denotes an integer from 1 to 10,
the radical R2 in each of the structural elements of formula (II) can be selected independently of the preceding structural element of formula (II),
R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, R3, R3' and R3", independently of each other, denote a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is a hair treatment agent with a cosmetic carrier containing (a) at least one compound of the general formula (I-IV)

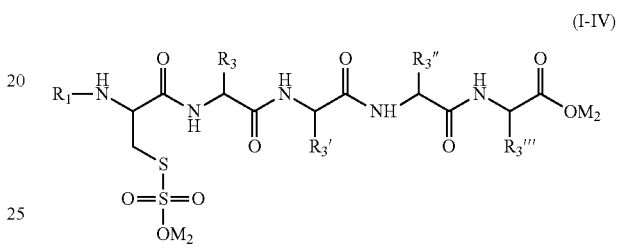

(I-IV)

wherein
R1 denotes a hydrogen atom or a structural element of formula (II)

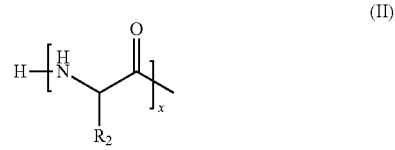

(II)

wherein
x denotes an integer from 1 to 10,
the radical R2 in each of the structural elements of formula (II) can be selected independently of the preceding structural element of formula (II),
R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, R3, R3', R3" and R3'", independently of each other, denote a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is a hair treatment agent with a cosmetic carrier containing (a) at least one compound of the general formula (I-V)

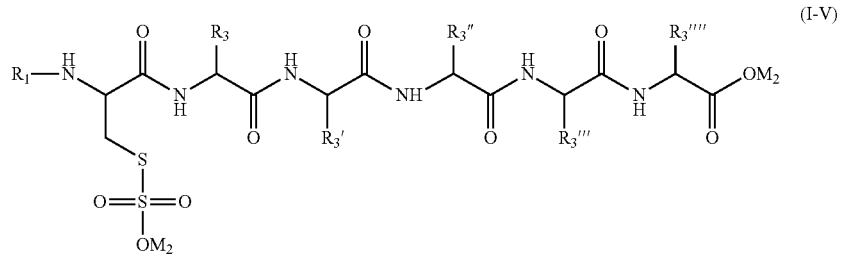
(I-V)

wherein
R1 denotes a hydrogen atom or a structural element of formula (II)

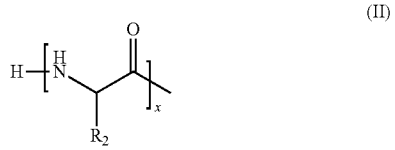
(II)

wherein
x denotes an integer from 1 to 10, the radical R2 in each of the structural elements of formula (II) can be selected independently of the preceding structural element of formula (II), R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, R3, R3', R3", R3''' and R3'''', independently of each other, denote a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is a hair treatment agent with a cosmetic carrier containing (a) at least one compound of the general formula (I-VI)

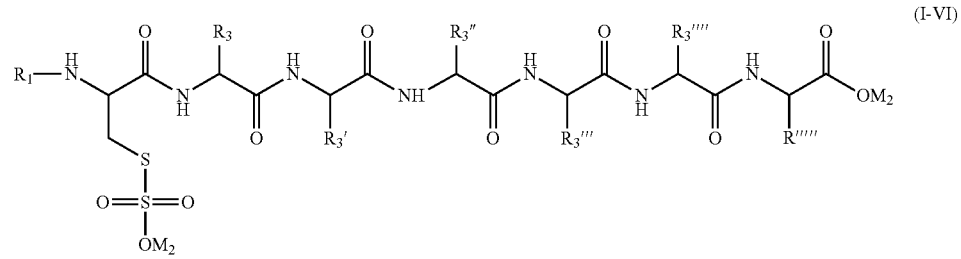
(I-VI)

wherein
R1 denotes a hydrogen atom or a structural element of formula (II)

(II)

wherein
x denotes an integer from 1 to 10,
the radical R2 in each of the structural elements of formula (II) can be selected independently of the preceding structural element of formula (II), R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, R3, R3', R3'', R3''', R3'''' and R3''''', independently of each other, denote a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

If the radical R3 denotes a hydrogen atom, the structural element of formula (II) is based on the amino acid glycine. If the radical R3 denotes a methyl group, the structural element of formula (II) is based on the amino acid alanine.

If the radical R3 denotes an isopropyl group (i.e. a group $(H_3C)_2CH-$), the structural element of formula (II) is based on the amino acid valine.

If the radical R3 denotes a 2-methylpropyl group (i.e. a group $(H_3C)_2CH-CH_2-$), the structural element of formula (II) is based on the amino acid leucine.

If the radical R3 denotes a 1-methyl-propyl group (i.e. a group H3C—CH2-CH(CH3)-), the structural element of formula (II) is based on the amino acid isoleucine.

If the radical R3 denotes a benzyl group (i.e. a group $C_6H_5-CH_2-$), the structural element of formula (II) is based on the amino acid phenylalanine.

If the radical R3 denotes a 4-hydroxybenzyl group (i.e. a group $4OH-C_6H_5-CH_2-$), the structural element of formula (II) is based on the amino acid tyrosine.

If the radical R3 denotes a hydroxymethyl group (i.e. a group HO—CH2-), the structural element of formula (II) is based on the amino acid serine.

If the radical R3 denotes a 1-hydroxyethyl group (i.e. a group H3C—CH(OH)—), the structural element of formula (II) is based on the amino acid threonine.

If the radical R3 denotes a 4-aminobutyl group (i.e. a group H2N—CH2-CH2-CH2-CH2-), the structural element of formula (II) is based on the amino acid lysine.

If the radical R3 denotes a 3-Carbamimidamidopropyl group (i.e. a group $H_2N-C(NH)-NH-CH_2-CH_2-CH_2-$), the structural element of formula (II) is based on the amino acid arginine.

If the radical R3 denotes a 2-carboxyethyl group (i.e. a group HOOC—CH2-CH2-), the structural element of formula (II) is based on the amino acid glutamic acid.

If the radical R3 denotes a carboxymethyl group (i.e. a group HOOC—CH2-), the structural element of formula (II) is based on the amino acid aspartic acid.

If the radical R3 denotes a 2-carbamoylethyl group (i.e. a group H2N—C(O)—CH2-CH2-), the structural element of formula (II) is based on the amino acid glutamine.

If the radical R3 denotes a carbamoylethyl group (i.e. a group H2N—C(O)—CH2-), the structural element of formula (II) is based on the amino acid Asparagine.

If the radical R3 denotes a sulfanylmethyl group (i.e. a group HS—CH2-), the structural element of formula (II) is based on the amino acid cysteine.

If the radical R3 denotes a 2-(methylsulfanyl)ethyl group (i.e. a group H3C—S—CH2-CH2-), the structural element of formula (II) is based on the amino acid methionine.

If the radical R3 denotes a 1H-imidazol-4-ylmethyl group, the structural element of formula (II) is based on the amino acid histidine.

If the radical R3 denotes a 1H-indol-3-ylmethyl group, the structural element of formula (II) is based on the amino acid tryptophan.

Finally, the radical R3 can also denote a (sulfosulfanyl) methyl group, in which case it is a functional group structure of formula HO—S(O2)—S—CH2—.

Depending on the pH value of the hair treatment agent, the functional group structure of formula HO—S(O2)—S—CH2— is also present in its deprotonated form.

The radical M2 denotes a hydrogen atom, an equivalent of one or more cations or an ammonia ion $(NH_4)^+$.

Preferred equivalents a mono- or multivalent cation can also be the cations of sodium and potassium $Na^+$ and $K^+$) or even magnesium or calcium (½ Mg2+ oder ½ Ca2+).

When M2 denotes a hydrogen atom, the grouping —OM2 is the grouping —OH. When M2 denotes a sodium cation, the grouping —OM2 is the grouping —ONa. When M2 denotes a potassium cation, the grouping —OM2 is the grouping —OK. When M2 denotes an ammonia, the grouping —OM2 is the grouping —O(NH4).

The inventive compounds of formula (I) are either the functional group of the amino acid cysteine, the bunt salts of oligopeptides or the functional groups of peptides.

If the radical R1 denotes a hydrogen atom and the radical M1 denotes a grouping —OM2, the compound of formula (I) is the functional group of the amino acid cysteine. In this case, the compound of formula (I) is the compound of formula (IA),

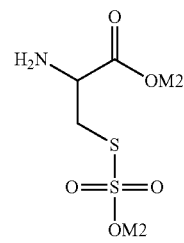

(IA)

where M2 is define as described above.

If the compound of formula (IA) is present in the form of its free acid, it is 2-amino-3-(sulfosulfanyl)propanoic acid. This substance is commercially available.

It has been found that use of the compound of formula (IA) in hair treatment agent already achieves an effective reduction of hair damage in particularly low amounts and is still present after repeated washing. Therefore, particular preference is given to use of compounds of formula (IA) in hair treatment agents.

In another embodiment, a hair treatment agent as contemplated herein exemplified (a) contains at least one compound of formula (I), wherein R1 denotes a hydrogen atom and
M1 denotes a —OM2 grouping.

When a compound of formula (IA) is used, it preferably uses this specific compound. However, when the functional groups of oligopeptides are used as compounds of formula (I), the inventive hair treatment agent also contain multiple compounds of formula (I) as a mixture of different oligopeptides. These oligopeptides are defined by their average molecular weight. The average molecular weight $M_w$ of the at least one oligopeptide of formula (I) can, for example, be determined by means of gel permeation chromatography (GPC) with polystyrene as an internal standard according to DIN 55672-3.

The molecular weight of the compound of formula (I) used as contemplated herein can vary depending on how many structural elements of formula (II) and/or (III) are contained in the compound of formula (I), and depending on these amino acids. As contemplated herein, it is most preferable for the compound of formula (I) to be an oligopeptide having a molecular weight $M_w$ of from about 200 to about 2,000 Da, preferably from about 250 to about 1,500 Da, more preferably from about 300 to about 1,200 Da, particularly from about 400 to about 800 Da.

In the context of the present disclosure, the term "oligopeptide" is understood to mean condensation products of amino acids having the aforementioned molecular weights.

A particularly preferred embodiment is an inventive hair treatment agent exemplified in that it contains a compound of formula (I) having a molecular weight $M_w$ of from about 200 to about 2,000 Da (Dalton), preferably from about 250 to about 1,500 Da, more preferably from about 300 to about 1,200 Da, particularly from about 400 to about 800 Da.

If a mixture of oligomers is used in the hair treatment agent as contemplated herein, these mixtures can be defined by their average molecular weight.

In this case, a preferred embodiment is an inventive hair treatment agent exemplified in that it contains at least on mixture of compounds of formula (I) having an average molecular weight $M_w$ of from about 200 to about 2,000 Da (Dalton), preferably from about 250 to about 1,500 Da, more preferably from about 300 to about 1,200 Da, particularly from about 400 to about 800 Da.

Furthermore, it has been found that the repair effect that the compounds of formula (I) have also depends on the repetition indices x and y. As described above, it is particularly preferred that x denotes an integer from 1 to 10 and y denotes an integer from 1 to 10.

In another more preferred embodiment, a hair treatment agent as contemplated herein iexemplified (a) contains at least one compound of formula (I), wherein
R1 denotes a structural element of formula (II), and
M1 denotes a structural element of formula (III), and
x denotes an integer from 1 to 10 and
y denotes an integer from 1 to 10.

In addition to the molecular weight of the compound of formula (I), the portion of functional group units contained in the compound of formula (I) has a decisive influence on the effectiveness of the "repair effect" of the compounds.

Compounds having at least one functional group unit—such as, for example, the compound of formula (Ia)—are very effective, particularly if they are used as a monomer compound. Oligopeptides having at least one functional group unit are particularly effective if they have a low molecular weight of up to 1200, particularly 800 Dalton.

However, with use of oligopeptides, it is particularly advantageous when the compound of formula (I) has at least two, preferably at least three functional group units.

In another more preferred embodiment, a hair treatment agent as contemplated herein exemplified (a) contains at least one compound of formula (I), wherein
R1 denotes a structural element of formula (II), and
the radical R2 denotes a (sulfosulfanyl)methyl group (i.e. a group HO—S(O$_2$)—S—CH$_2$—) in at least one structural element of formula (II).

A particularly preferred embodiment as contemplated herein is a hair treatment agent with a cosmetic carrier containing
(a) at least one compound of the general formula (I-a')

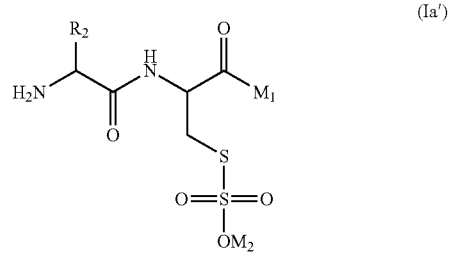

wherein
R2 denotes a (sulfosulfanyl)methyl group (i.e. a group HO—S(O$_2$)—S—CH$_2$—) and
M1 denotes the grouping —OM2 or a structural element of formula (III)

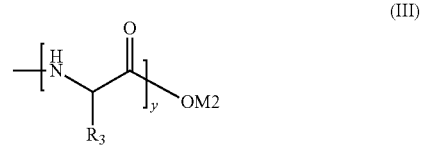

wherein
y denotes an integer from 1 to 10,
the radical R3 in each of the structural elements of formula (III) can be selected independently of the preceding structural element of formula (III),
R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 denotes a hydrogen atom, an equivalent of one or more cations or an ammonia ion (NH$_4$)$^+$.

A particularly preferred embodiment as contemplated herein is also a hair treatment agent with a cosmetic carrier containing
(a) at least one compound of the general formula (I-b')

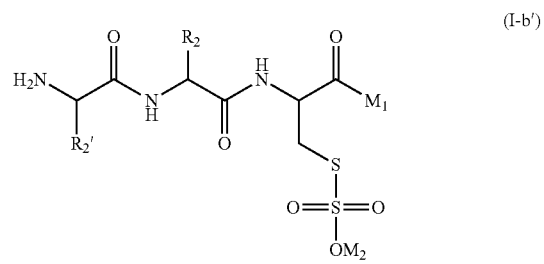

wherein one of radicals R2 and R2' denotes a (sulfosulfanyl)methyl group (i.e. a group HO—S(O₂)—S—CH₂—) and the other radical of R2 and R2' denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

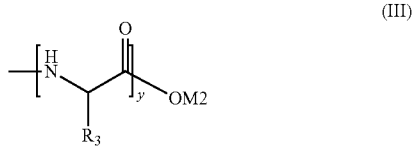

(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I-c')

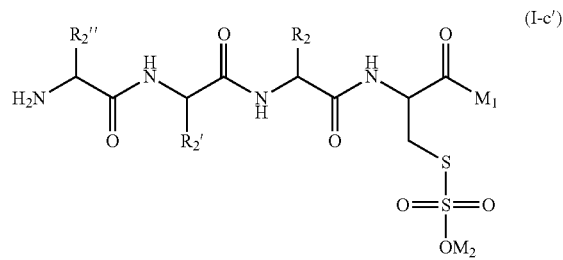

(I-c')

wherein one of radicals R2, R2' and R2" denotes a (sulfosulfanyl)methyl group (i.e. a group HO—S(O₂)—S—CH₂—) and the other two radicals of R2, R2' and R2", independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

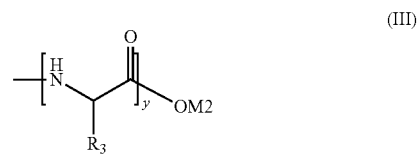

(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I-d')

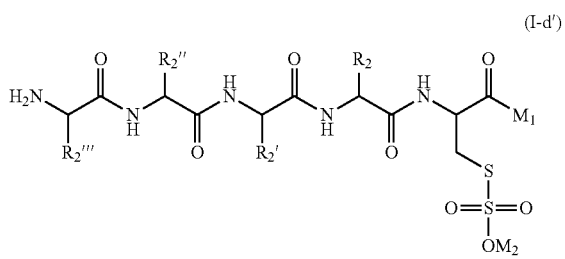

(I-d')

wherein one of radicals R2, R2', R2" and R2'" denotes a (sulfosulfanyl)methyl group (i.e. a group HO—S(O₂)—S—CH₂—) and the other three radicals of R2, R2', R" and R2'", independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

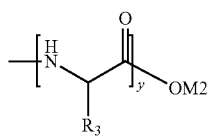

(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I-e')

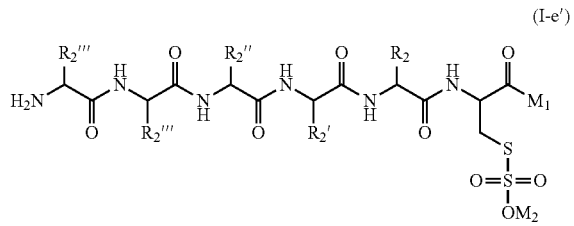

wherein one of radicals R2, R2', R2'', R2''' and R2'''' denotes a (sulfosulfanyl)methyl group (i.e. a group HO—S($O_2$)—S—$CH_2$—) and the other four radicals of R2, R2', R2'', R2''' and R2'''', independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

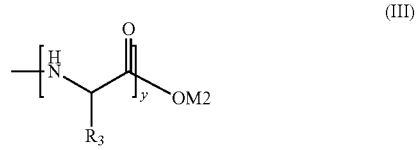

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I-f')

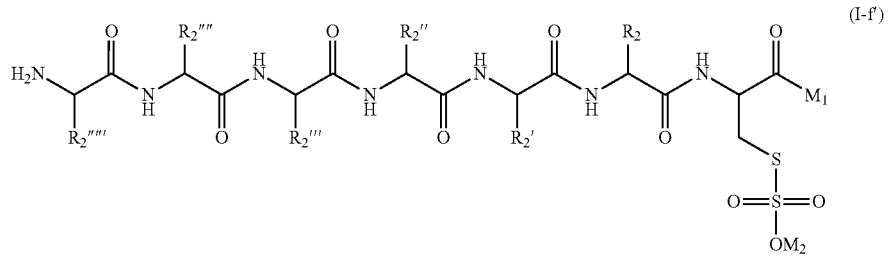

wherein one of radicals R2, R2', R2'', R2''', R2'''' and R2''''' denotes a (sulfosulfanyl)methyl group (i.e. a group HO—S($O_2$)—S—$CH_2$—) and the other five radicals of R2, R2', R2'', R2''', R2'''' and R2''''', independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

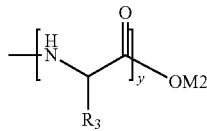

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

In another more preferred embodiment, a hair treatment agent as contemplated herein exemplified (a) contains at least one compound of formula (I), wherein R1 denotes a structural element of formula (II), and x denotes an integer from 1 to 10 and the radical R2 denotes a 2-carboxyethylgroup (i.e. a group HOOC—CH2-CH2-) in at least one structural element of formula (II).

A particularly preferred embodiment as contemplated herein is a hair treatment agent with a cosmetic carrier containing (a) at least one compound of the general formula (I-a″)

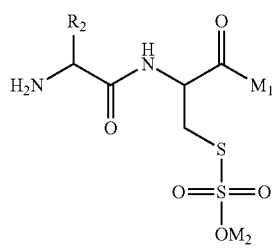

wherein

R2 denotes a 2-carboxyethyl group (i.e. a group HOOC—CH2-CH2-), and

M1 denotes the grouping —OM2 or a structural element of formula (III)

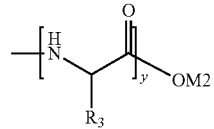

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I-b″)

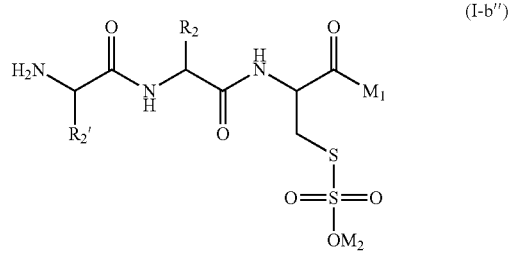

wherein one of radicals R2 and R2′ denotes a 2-carboxyethyl group (i.e. a group HOOC—CH2-CH2-) and the other radical of R2 and R2′ denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

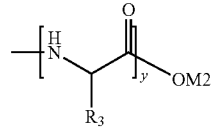

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I-c″)

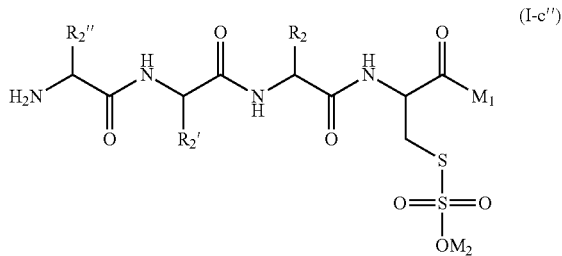

(I-c″)

wherein one of radicals R2, R2' and R2″ denotes a 2-carboxyethyl group (i.e. a group HOOC—CH2-CH2-) and the other two radicals of R2, R2' and R2″, independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

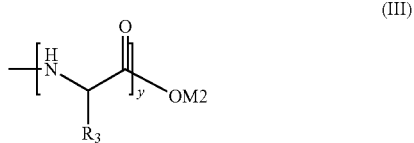

(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I-d″)

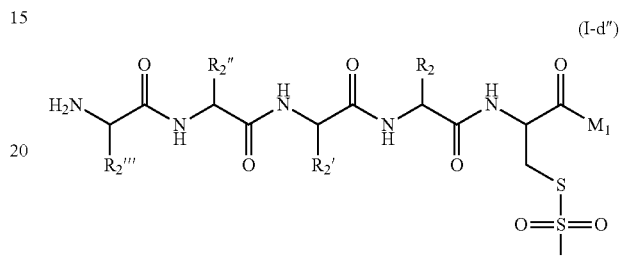

(I-d″)

wherein one of radicals R2, R2', R2″ and R2‴ denotes a 2-carboxyethyl group (i.e. a group HOOC—CH2-CH2-) and the other three radicals of R2, R2', R″ and R2‴, independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

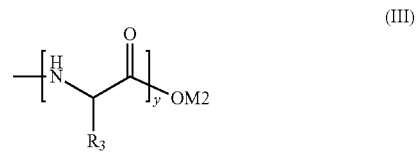

(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I-e'')

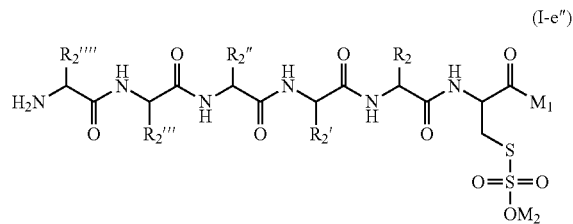

(I-e'')

wherein one of radicals R2, R2', R2'', R2''' and R2'''' denotes a 2-carboxyethyl group (i.e. a group HOOC—CH2-CH2-) and the other four radicals of R2, R2', R2'', R2''' and R2'''', independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

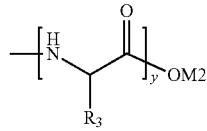

(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I-f')

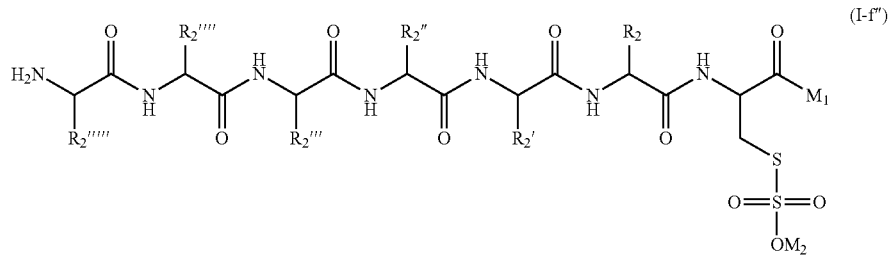

(I-f'')

wherein one of radicals R2, R2', R2'', R2''', R2'''' and R2''''' denotes a 2-carboxyethyl group (i.e. a group HOOC—CH2-CH2-) and the other five radicals of R2, R2', R2'', R2''', R2'''' and R2''''', independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

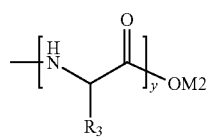

(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

In another more preferred embodiment, a hair treatment agent as contemplated herein exemplified (a) contains at least one compound of formula (I), wherein M1 denotes a structural element of formula (III), and the radical R3 denotes a (sulfosulfanyl)methyl group (i.e. a group $HO-S(O_2)-S-CH_2-$) in at least one structural element of formula (III).

A particularly preferred embodiment as contemplated herein is a hair treatment agent with a cosmetic carrier containing (a) at least one compound of the general formula (I-I')

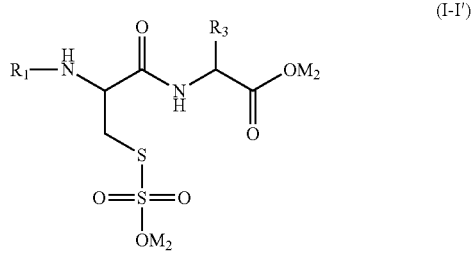

wherein

R1 denotes a hydrogen atom or a structural element of formula (II)

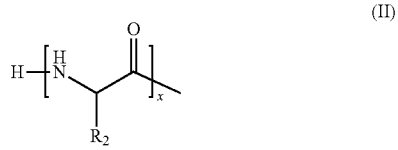

wherein x denotes an integer from 1 to 10, the radical R2 in each of the structural elements of formula (II) can be selected independently of the preceding structural element of formula (II), R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, R3 denotes a (sulfosulfanyl)methyl group (i.e. a group $HO-S(O_2)-S-CH_2-$) and M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula

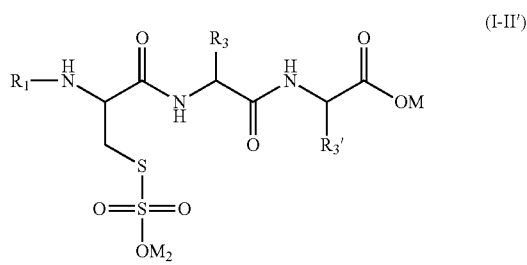

wherein

R1 denotes a hydrogen atom or a structural element of formula (II)

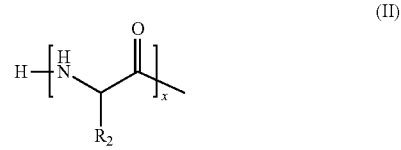

wherein x denotes an integer from 1 to 10, the radical R2 in each of the structural elements of formula (II) can be selected independently of the preceding structural element of formula (II), R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, one of radicals R3 and R3' denotes a (sulfosulfanyl)methyl group (i.e. a group $HO-S(O_2)-S-CH_2-$) and the other radicals of R3 and R3', independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$. A particularly preferred embodiment as contemplated herein is a hair treatment agent with a cosmetic carrier containing (a) at least one compound of the general formula (I-III')

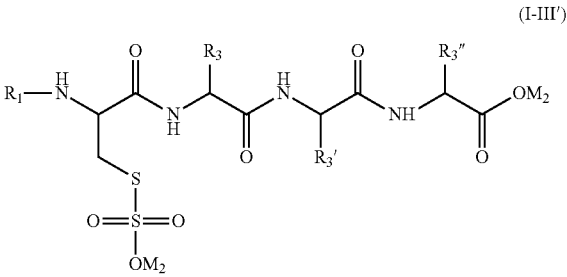

wherein
R1 denotes a hydrogen atom or a structural element of formula (II)

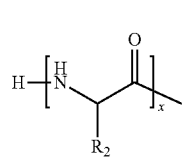
(II)

wherein
x denotes an integer from 1 to 10,
the radical R2 in each of the structural elements of formula (II) can be selected independently of the preceding structural element of formula (II),
R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, one of radicals R3, R3' and R3" denotes a (sulfosulfanyl)methyl group (i.e. a group HO—S(O$_2$)—S—CH$_2$—) and the other radicals of R3, R3' and R3", independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion (NH$_4$)$^+$.

A particularly preferred embodiment as contemplated herein is a hair treatment agent with a cosmetic carrier containing
(a) at least one compound of the general formula (I-IV')

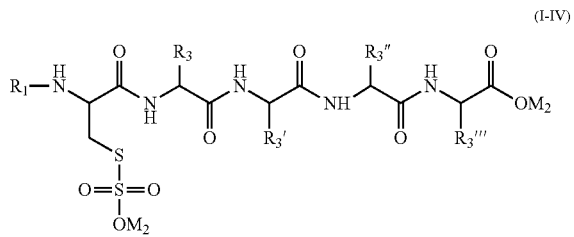
(I-IV)

wherein
R1 denotes a hydrogen atom or a structural element of formula (II)

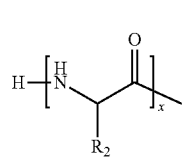
(II)

wherein
x denotes an integer from 1 to 10,
the radical R2 in each of the structural elements of formula (II) can be selected independently of the preceding structural element of formula (II),
R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, one of radicals R3, R3', R3" and R3'" denotes a (sulfosulfanyl)methyl group (i.e. a group HO—S(O$_2$)—S—CH$_2$—) and the other radicals of R3, R3', R3" and R3'", independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion (NH$_4$)$^+$.

A particularly preferred embodiment as contemplated herein is a hair treatment agent with a cosmetic carrier containing
(a) at least one compound of the general formula (I-V')

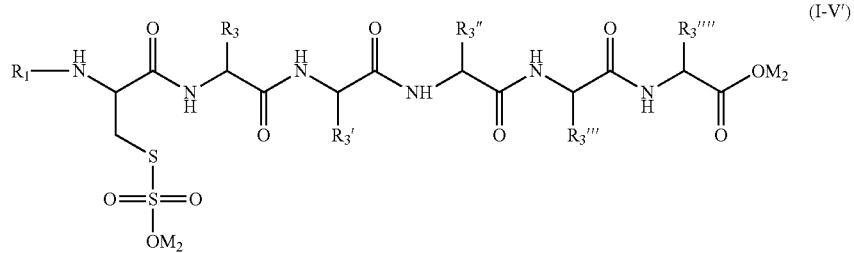
(I-V')

wherein
R1 denotes a hydrogen atom or a structural element of formula (II)

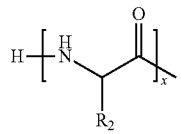
(II)

wherein
x denotes an integer from 1 to 10,
the radical R2 in each of the structural elements of formula (II) can be selected independently of the preceding structural element of formula (II),
R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
one of radicals R3, R3', R3", R3"' and R3"" denotes a (sulfosulfanyl)methyl group (i.e. a group HO—S(O₂)—S—CH₂—) and
the other radicals of R3, R3', R3", R3"' and R3"", independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 denotes a hydrogen atom, an equivalent of one or more cations or an ammonia ion (NH₄)⁺. A particularly preferred embodiment as contemplated herein is a hair treatment agent with a cosmetic carrier containing
(a) at least one compound of the general formula (I-VI')

wherein
R1 denotes a hydrogen atom or a structural element of formula (II)

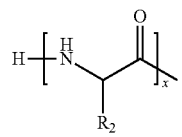
(II)

wherein
x denotes an integer from 1 to 10,
the radical R2 in each of the structural elements of formula (II) can be selected independently of the preceding structural element of formula (II),
R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, one of radicals R3, R3', R3", R3"', R"" and R3"" denotes a (sulfosulfanyl)methyl group (i.e. a group HO—S(O₂)—S—CH₂—) and
the other radicals of R3, R3', R3", R3"", R3"" and R3"", independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 denotes a hydrogen atom, an equivalent of one or more cations or an ammonia ion (NH₄)⁺.
In another more preferred embodiment, a hair treatment agent as contemplated herein exemplified (a) contains at least one compound of formula (I), wherein
R1 denotes a structural element of formula (II), and
x denotes an integer from at least 3 and
the radical R2 denotes a 2-carboxyethylgroup (i.e. a group HOOC—CH2-CH2-) in at least 3 structural elements of formula (II).
A particularly preferred embodiment as contemplated herein is also a hair treatment agent with a cosmetic carrier containing

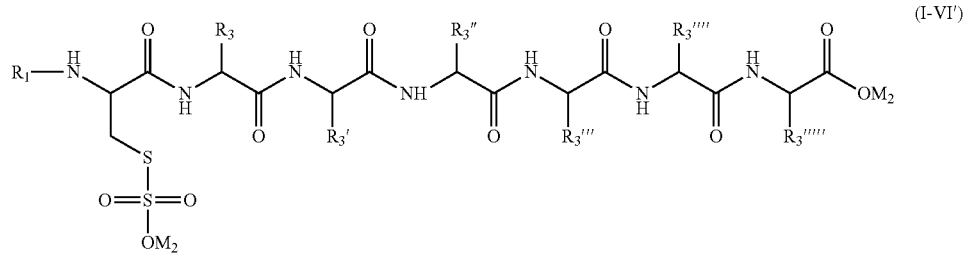
(I-VI')

(a) at least one compound of the general formula (I)

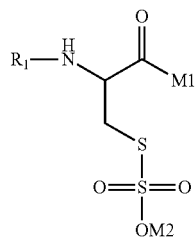

wherein
R1 denotes a structural element of formula (II)

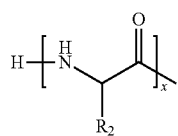

wherein
x denotes an integer from 3 to 10
the radical R2 in each of the structural elements of formula (II) can be selected independently of the preceding structural element of formula (II),
the radical R2 denotes a 2-carboxyethylgroup (i.e. a group HOOC—CH2-CH2-) in at least 3 structural elements of formula (II) and
the radical R2 in the remaining structural elements of formula (II) denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M1 denotes a structural element of formula (III)

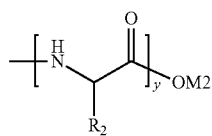

wherein
y denotes an integer from 1 to 10,
the radical R3 in each of the structural elements of formula (III) can be selected independently of the preceding structural element of formula (III),
R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 denotes a hydrogen atom, an equivalent of one or more cations or an ammonia ion $(NH_4)^+$.

In another more preferred embodiment, a hair treatment agent as contemplated herein exemplified (a) contains at least one compound of formula (I), wherein
M1 denotes a structural element of formula (III), and
y denotes an integer from at least 1 to 10 and
the radical R3 denotes a 2-carboxyethylgroup (i.e. a group HOOC—CH2-CH2-) in at least one structural element of formula (III).

A particularly preferred embodiment as contemplated herein is a hair treatment agent with a cosmetic carrier containing
(a) at least one compound of the general formula (I-I″)

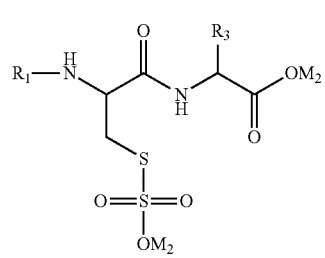

wherein
R1 denotes a hydrogen atom or a structural element of formula (II)

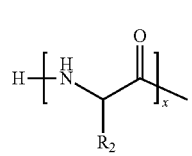

wherein
x denotes an integer from 1 to 10,
the radical R2 in each of the structural elements of formula (II) can be selected independently of the preceding structural element of formula (II),
R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
R3 denotes a 2-carboxyethyl group (i.e. a group HOOC—CH2-CH2-), and
M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I-II")

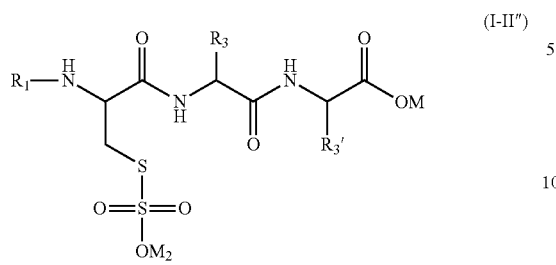

wherein
R1 denotes a hydrogen atom or a structural element of formula (II)

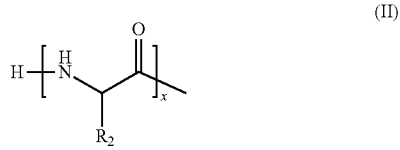

wherein
x denotes an integer from 1 to 10,
the radical R2 in each of the structural elements of formula (II) can be selected independently of the preceding structural element of formula (II),
R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, one of radicals R3 and R3' denotes a 2-carboxyethyl group (i.e. a group HOOC—CH2-CH2-) and
the other radicals of R3 and R3', independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 denotes a hydrogen atom, an equivalent of one or more cations or an ammonia ion $(NH_4)^+$.
A particularly preferred embodiment as contemplated herein is a hair treatment agent with a cosmetic carrier containing
(a) at least one compound of the general formula (I-III")

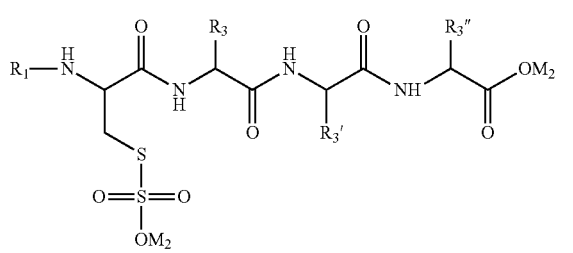

wherein
R1 denotes a hydrogen atom or a structural element of formula (II)

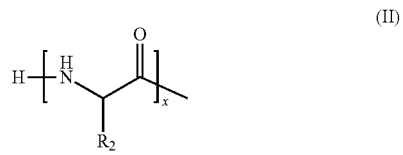

wherein
x denotes an integer from 1 to 10,
the radical R2 in each of the structural elements of formula (II) can be selected independently of the preceding structural element of formula (II),
R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
one of radicals R3, R3' and R3" denotes a 2-carboxyethyl group (i.e. a group HOOC—CH2-CH2-) and
the other radicals of R3, R3' and R3", independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 denotes a hydrogen atom, an equivalent of one or more cations or an ammonia ion $(NH_4)^+$.
A particularly preferred embodiment as contemplated herein is a hair treatment agent with a cosmetic carrier containing
(a) at least one compound of the general formula (I-IV")

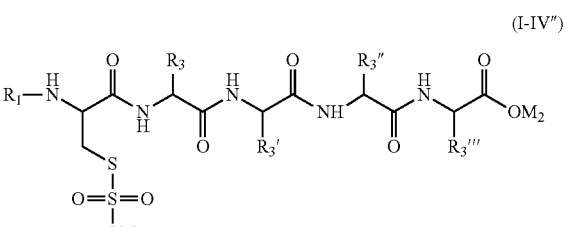

wherein
R1 denotes a hydrogen atom or a structural element of formula (II)

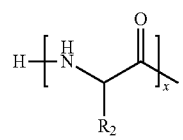
(II)

wherein x denotes an integer from 1 to 10, the radical R2 in each of the structural elements of formula (II) can be selected independently of the preceding structural element of formula (II), R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, one of radicals R3, R3', R3" and R3'" denotes a 2-carboxyethyl group (i.e. a group HOOC—CH2-CH2-) and the other radicals of R3, R3', R3" and R3'", independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl) methyl group, M2 denotes a hydrogen atom, an equivalent of one or more cations or an ammonia ion $(NH_4)^+$.

A particularly preferred embodiment as contemplated herein is a hair treatment agent with a cosmetic carrier containing (a) at least one compound of the general formula (I-V")

wherein

R1 denotes a hydrogen atom or a structural element of formula (II)

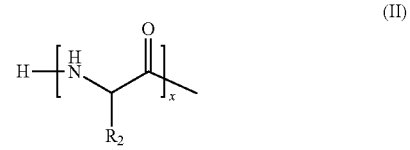
(II)

wherein x denotes an integer from 1 to 10, the radical R2 in each of the structural elements of formula (II) can be selected independently of the preceding structural element of formula (II), R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, one of radicals R3, R3', R3", R3'" and R3"" denotes a 2-carboxyethyl group (i.e. a group HOOC—CH2-CH2-) and the other radicals of R3, R3', R3", R3'" and R3"", independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is a hair treatment agent with a cosmetic carrier containing

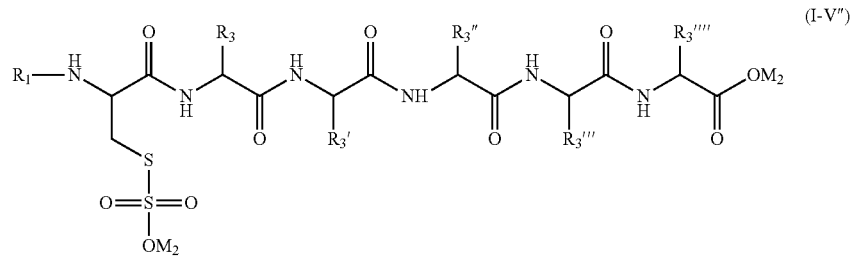
(I-V")

(a) at least one compound of the general formula (I-VI″)

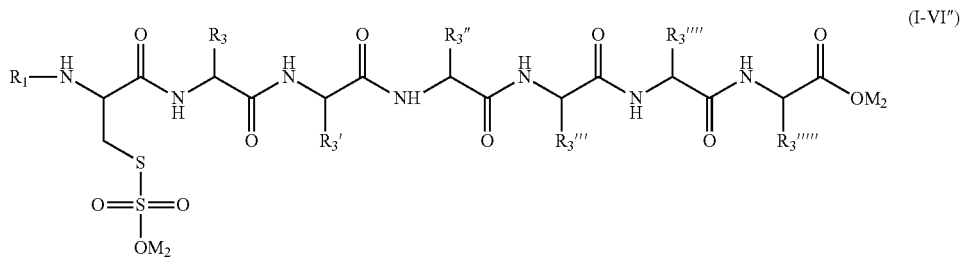

wherein

R1 denotes a hydrogen atom or a structural element of formula (II)

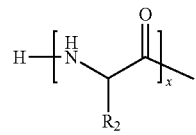

wherein x denotes an integer from 1 to 10, the radical R2 in each of the structural elements of formula (II) can be selected independently of the preceding structural element of formula (II), R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, one of radicals R3, R3', R3″, R3‴, R3⁗ and R3⁗′ denotes a 2-carboxyethyl group (i.e. a group HOOC—CH2-CH2-) and the other radicals of R3, R3', R3″, R3‴, R3⁗ and R3⁗′, independently of each other, denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion (NH4)+.

In another more preferred embodiment, a hair treatment agent as contemplated herein exemplified (a) contains at least one compound of formula (I), wherein M1 denotes a structural element of formula (III), and y denotes an integer from at least 3 and the radical R3 denotes a 2-carboxyethyl group in at least 3 structural elements of formula (III).

A particularly preferred embodiment as contemplated herein is also a hair treatment agent with a cosmetic carrier containing (a) at least one compound of the general formula (I)

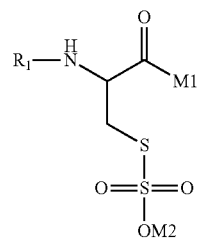

wherein

R1 denotes a structural element of formula (II)

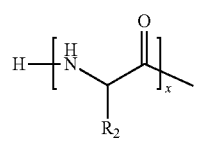

wherein x denotes an integer from 1 to 10, the radical R2 in each of the structural elements of formula (II) can be selected independently of the preceding structural element of formula (II), R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes a structural element of formula (III)

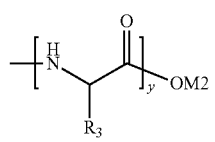

wherein y denotes an integer from 3 to 10, the radical R3 in each of the structural elements of formula (III) can be selected independently of the preceding structural element of formula (III), the radical R3 denotes a 2-carboxyethylgroup (i.e. a group HOOC—CH2-CH2-) in at least three structural elements of formula (III), and the radical R3 in the remaining structural elements of formula (III) denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I)

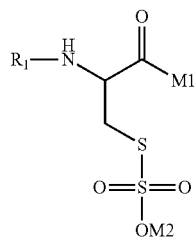

(I)

wherein
R1 denotes a structural element of formula (II)

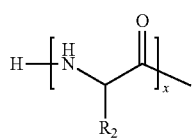

(II)

wherein x denotes an integer from 8 to 10, the radical R2 in each of the structural elements of formula (II) can be selected independently of the preceding structural element of formula (II), one of the R2 radicals denotes a 2-methylpropyl group and one of the R2 radicals denotes an isopropyl group and one of the R2 radicals denotes a 3-carbimidamidopropyl group (i.e. a group $H_2N$—$C(NH)$—$NH$—$CH_2$—$CH_2$—$CH_2$—) and one of the R2 radicals denotes a 1-methylpropyl group (i.e. a group $H3C$—$CH2$-$CH(CH3)$-) and three of the R2 radicals denote a 2-carboxyethyl group (i.e. a group HOOC—CH2-CH2-), and one of the R2 radicals denotes a 4-hydroxybenzyl group (i.e. a group 4-OH—$C_6H_5$—$CH_2$—)

the other R2 radicals denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes the grouping —OM2 or a structural element of formula (III)

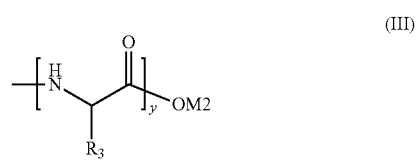

(III)

wherein y denotes an integer from 1 to 10, the radical R3 in each of the structural elements of formula (III) can be selected independently of the preceding structural element of formula (III), R3 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion $(NH_4)^+$.

A particularly preferred embodiment as contemplated herein is also a hair treatment agent with a cosmetic carrier containing (a) at least one compound of the general formula (I)

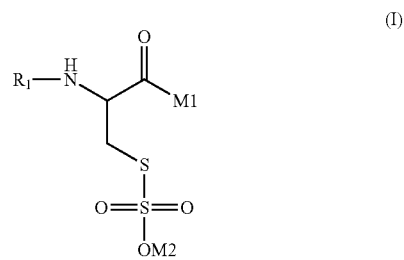

(I)

wherein
R1 denotes a hydrogen atom or a structural element of formula (II)

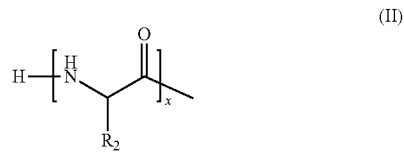

(II)

wherein x denotes an integer from 1 to 10, the radical R2 in each of the structural elements of formula (II) can be selected independently of the preceding structural element of formula (II), R2 denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 denotes a structural element of formula (III)

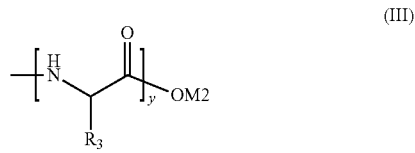

(III)

wherein y denotes an integer from 8 to 10, the radical R3 in each of the structural elements of formula (III) can be selected independently of the preceding structural element of formula (III), one of the R3 radicals denotes a 2-methylpropyl group and one of the R3 radicals denotes an isopropyl group and one of the R3 radicals denotes a 3-carbimidamidopropyl group (i.e. a group H$_2$N—C(NH)—NH—CH$_2$—CH$_2$—CH$_2$—) and one of the R3 radicals denotes a 1-methylpropyl group (i.e. a group H3C—CH2-CH(CH3)-) and three of the R3 radicals denote a 2-carboxyethyl group (i.e. a group HOOC—CH2-CH2-), and one of the R3 radicals denotes a 4-hydroxybenzyl group (i.e. a group 4-OH—C$_6$H$_5$—CH$_2$—)

the other R3 radicals denote a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 denotes a hydrogen atom, an equivalent of one or more cations or an ammonia ion (NH$_4$)$^+$.

The compounds of formula (I) can be use in a total amount of from about 0.0001 to about 10 wt. % relative to the total weight of the hair treatment agent. Surprisingly, it has been found that the compound(s) of formula (I) can achieve a very good reduction of hair damage already in low usage concentrations. This entails the particularly advantage that the inventive hair treatment agent should be added to an already existing product as an additive (for example, as care drops or a care cream). For this reason, it is particularly advantageous that the inventive hair treatment agent contains one or multiple compounds of formula (I) in a total amount of from about 0.001 to about 10.0 wt. %, preferably from about 0.01 to about 2.5 wt. %, more preferably from about 0.05 to about 1.0 wt. % and particularly from about 0.05 to about 0.3 wt. %.

In another particularly preferred embodiment a hair treatment agent as contemplated herein contains one or multiple compounds of formula (I) in a total amount of from about 0.0001 to about 10.0 wt. %, preferably from about 0.001 to about 10.0 wt. %, more preferably from about 0.01 to about 2.5 wt. %, even more preferably from about 0.05 to about 1.0 wt. % and particularly from about 0.05 to about 0.3 wt. %.

In principle, the inventive hair treatment agent can be used in a wide variety of application forms, such as shampoo, conditioner, a care additive, gel or aerosol. In the context of the work carried out for this present disclosure, however, it was discovered that the compounds of formula (I) are particularly suitable when used in an oxidative hair treatment agent, such as an oxidative dyeing agent or a bleaching agent.

Oxidative hair treatment agents are exemplified by the presence of at least one oxidant. The oxidant is preferably hydrogen peroxide and/or one of its addition products of organic or inorganic compounds, such as urea, melamine and sodium borate. Particular preference is given to hydrogen peroxide as the oxidant.

In a further particularly preferred embodiment, a hair treatment agent as contemplated herein is exemplified it also (b) contains hydrogen peroxide as an oxidant.

Preferably, the amount of oxidants in the agent as contemplated herein is from about 0.5 to about 12 wt. %, more preferably from about 2 to about 10 wt. %, particularly from about 3 to about 6 wt. % (calculated as 100% H$_2$O$_2$), relative to the total weight of the ready-to-use agent in each case.

When the inventive hair treatment agent is an oxidative dye, oxidation dye precursors can also be contained in the inventive agent.

Oxidation dye precursors are so-called developer components and coupler components. The developer components join together or couple with one or more coupler components to form, under the influence of oxidants or atmospheric oxygen, the actual dyes per se.

In a further particularly preferred embodiment, an inventive hair treatment agent is exemplified it contains (a) at least one compound of formula (I) and (b) hydrogen peroxide and (c) at least one oxidation dye precursor.

Other preferred developer components are selected from p-phenylendiamine, p-toluylendiamine, 2-(2-hydroxyethyl)-p-phenylendiamine, 2-(1,2-dihydroxyethyl)-p-phenylendiamin, N,N-bis-(2-hydroxyethyl)-p-phenylendiamine, 2-methoxymethyl-p-phenylendiamine, N-(4-amino-3-methylphenyl)-N-[3-(1H-imidazol-1-yl)propyl]amine, N,N'-bis-(2-hydroxyethyl)-N,N-bis-(4-aminophenyl)-1,3-diamino-propane-2-ol, bis-(2-hydroxy-5-aminophenyl)methane, 1,3-bis-(2,5-diaminophenoxy)propane-2-ol, N,N'-bis-(4-aminophenyl)-1,4-diazacycloheptane, 1,10-bis-(2,5-diaminophenyl)-1,4,7,10-tetraoxadecane, 4-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazol, 2,4,5,6-tetraaminopyrimidine, 4-hydroxy-2,5,6-triaminopyrimidine, 2-hydroxy-4,5,6-triaminopyrimidine, the physiologically tolerated salts of said compounds. Additional particularly preferred developer components are p-toluylendiamine, 2-(2-hydroxyethyl)-p-phenylen-diamine, 2-methoxymethyl-p-phenylendiamine, N-(4-amino-3-methylphenyl)-N-[3-(1H-imidazol-1-yl)-propyl)amine, and/oder 4,5-diamino-1-(2-hydroxyethyl)pyrazole, as well as the physiologically-tolerable salts thereof.

Preferred couplers can be selected from the group of 3-aminophenol, 5-amino-2-methylphenol, 3-amino-2-chlor-6-methylphenol, 2-hydroxy-4-aminophenoxyethanol, 5-amino-4-chlor-2-methylphenol, 5-(2-hydroxyethyl)-amino-2-methylphenol, 2,4-dichlor-3-aminophenol, 2-aminophenol, 3-phenylendiamine, 2-(2,4-diaminophenoxy)ethanol, 1,3-bis(2,4-diaminophenoxy)propane, 1-methoxy-2-amino-4-(2-hydroxyethylamino)benzol (2-amino-4-[(2-hydroxyethyl)amino]-anisol), 1,3-bis(2,4-diaminophenyl)propane, 2,6-bis(2'-hydroxyethylamino)-1-methylbenzol, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzol, resorcin, 2-methylresorcin, 4-chlorresorcin, 1,2,4-trihydroxybenzol, 2-amino-3-hydroxypyridin, 3-amino-2-methylamino-6-methoxypyridin, 2,6-dihydroxy-3,4-dimethylpyridin, 3,5-diamino-2,6-dimethoxypyridin, 1-phenyl-3-methylpyrazol-5-on, 1-naphthol, 1,5-dihydroxynaphthalin, 2,7-dihydroxynaphthalin, 1,7-dihydroxynaphthalin, 1,8-dihydroxynaphthalin, 4-hydroxyindol, 6-hydroxyindol, 7-hydroxyindol, 4-hydroxyindolin, 6-hydroxyindolin, 7-hydroxyindolin or mixtures of said compounds or the physiologically compatible salts thereof.

Particularly good effects were observed when the inventive agent was used in combination with persulfates, i.e. in an oxidative bleaching agent. In this context, it has been found that the reduction of hair damage was surprisingly long-lasting and the "hair-repair" effect did not diminish even after repeated washing.

In an explicitly particularly preferred embodiment, an inventive hair treatment agent is
exemplified it also
(b) contains at least one peroxide compound as an oxidant from the group of hydrogen peroxide, ammonium peroxodisulfate, potassium peroxodisulfate and/or sodium peroxodisulfate.

In a further particularly preferred embodiment, an inventive hair treatment agent is exemplified it contains
(a) at least one compound of formula (I) and
(b1) hydrogen peroxide and
(b2) contains at least one peroxide compound as from the group of hydrogen peroxide, ammonium peroxodisulfate, potassium peroxodisulfate and/or sodium peroxodisulfate. The latter embodiment is the most preferred embodiment.

Potassium peroxodisulfate is also referred to as potassium persulfate and has the empirical formula $K_2S_2O_8$.

Ammonium peroxodisulfate is also referred to as potassium persulfate and has the empirical formula $(NH_4)_2S_2O_8$.

Sodium peroxodisulfate is also referred to as potassium persulfate and has the empirical formula $Na_2S_2O_8$.

Furthermore, it has been found that the weight ratio in which the (a) compound(s) of formula (I) and (b) contain the oxidant or oxidants in a hair treatment agent influences the magnitude of the repair effect. With selection of the optimal ratio, the repair effect can be even further optimized.

Particularly good effects, i.e. a particularly strong reduction of hair damaged, were observed when the hair treatment agent (a) contains the compound(s) of formula (I) and (b) the oxidant is contained in a weight ratio (a)/(b) of about 1:20, preferably about 1:15, more preferably about 1:10, particularly about 1:8. In other words, the reduction of hair damage was particularly strong when the hair treatment agent contains the oxidant (b) in an amount of about 8 to about 20 times the amount (a) of the compound or compounds of formula (I).

In an explicitly particularly preferred embodiment, an inventive hair treatment agent contains (a) the compound(s) of formula (I) and (b) the oxidant is contained in a weight ratio (a)/(b) of about 1:20, preferably about 1:15, more preferably about 1:10, particularly 1:8.

The basis for calculation of the weight ratio (a)/(b) is the total amount of all compounds (a) of formula (I) contained in the agent used in relation to the total weight of all oxidants (b) contained in the agent (hydrogen peroxide, ammonium peroxodisulfate, potassium peroxodisulfate and sodium peroxodisulfate).

The inventive oxidative hair treatment agent, which also contains one or multiple (b) oxidants in addition to (a) the compounds of formula (I), the consumer is available to the consumer in an optimal manner in the form of a kit (a multi-component kit-of-parts). To avoid incompatibilities and increase storage stability, (a) the compounds of formula (I) and (b) the oxidant or oxidants are not mixed together until immediately before use. Therefore, the inventive kit comprises at least two separately packaged preparations.

A further subject of the present disclosure is a kit for oxidative dyeing and/or lightening of hair containing at least two separately packaged preparations (A) and (B), wherein
preparation (A) is an agent that contains a compound of formula (I), as disclosed in the description of the first subject of the present disclosure,
preparation (B) is an oxidant preparation containing at least one oxidant from the group of ammonia peroxodisulfate, potassium peroxodisulfate and sodium peroxodisulfate.

A further subject of the present disclosure is a kit for oxidative dyeing and/or lightening of hair containing at least two separately packaged preparations (A) and (B), wherein
preparation (A) is an agent that contains a compound of formula (I), as disclosed in the description of the first subject of the present disclosure,
preparation (B) is an oxidant preparation containing hydrogen peroxide.

To produce the ready-to-use oxidative dyeing and/or lightening agent, preparations (A) and (B) can be mixed with each other in a weight ratio of from about 1:10 to about 10:1. It is particularly advantageous with respect to optimal lightening and dyeing when preparations (A) and (B) are mixed in a (A)/(B) ratio of from about 3:1 to about 1:3, preferably from about 2:1 to about 1:2 and particularly from about 1.5:1 to about 1:1.5.

In another particularly preferred embodiment, an inventive kitexemplified of at least three separately packaged preparations (A), (B1) and (B2), wherein
preparation (A) contains the at least one compound of formula (I),
preparation (B1) is an oxidant preparation containing hydrogen peroxide,
preparation (B2) is an oxidant preparation containing at least one oxidant from the group of ammonia peroxodisulfate, potassium peroxodisulfate and sodium peroxodisulfate.

To produce the ready-to-use oxidative lightening agent, preparations (A), (B1) and (B2) can be mixed with each other in a weight ratio of
from about 1 to about 10 weight portions of preparation (A) and from about 1 to about 10 weight portions of preparation (B1) and from about 1 to 1 about 0 weight portions of preparation (B2)

The inventive hair treatment agents or inventive preparations (A), (B) or ((B1) and (B2)) can each contain additional ingredients, active ingredients and additives.

The agents as contemplated herein can additionally contain other organic solvents, such as methoxybutanol, ethyldiglycol, 1,2-propylenglycol, n-propanol, n-butanol, n-butylenglycol, glycerine, diethylenglycolmonoethylether, and Diethylenglycolmono-n-butylether. All water-soluble organic solvents are preferred, wherein the solvent is contained in a total quantity of from about 0.1 to about 30 wt. %, preferably from about 1 to about 20 wt. %, more particularly from about 2 to about 10 wt. %, relative to the total weight of the cosmetic agent.

The cosmetic agents as contemplated herein can also contain an additional conditioning substance selected from the group of cationic polymers, cationic surfactants, silicones, fatty substances and mixtures thereof. The term "conditioning substances" is understood to mean substances applied to keratinous materials, particularly the hair, and improve the physical and sensory characteristics of the hair and the product as such. Conditioning agents smooth the top layer of the hair and make is soft and supple.

Preferred cationic polymers are selected from the group of oly(methacryloyloxyethyltrimethylammoniumchloride) (INCI: PolyQuaternium-37), quatemated cellulose derivatives (INCI: Polyquatemium 10) cationic alkyl polyglycosides, cationized honey, cationic guar derivatives, polymeric dimethyldiallylammonium salts and copolymers thereof with esters and amides of acrylic acid and methacrylic acid, copolymers of vinylpyrrolidone with quaternized derivatives of dialkylaminoalkyl acrylate and methacrylate, vinylpyrrolidone-vinylimidazolium methochloride copolymers, quaternized polyvinyl alcohol, Polyquaternium 2, Polyquaternium 7, Polyquaternium 17, Polyquaternium 18, Polyquaternium 24, Polyquatemium 27 and mixtures thereof.

In the context of the present disclosure, it can be advantageous when the cationic polymer(s) are contained in a total amount of from about 0.05 to about 7.5 wt. %, preferably from about 0.1 to about 5 wt. %, more preferably from about 0.2 to about 3.5 wt. %, particularly from about 0.25 to about 2.5 wt. % relative to the total weight of the cosmetic agent used as contemplated herein.

In the context of the present disclosure, cationic surfactants from the group of quaternary ammonia compounds and/or esterquats and amidoamines are suitable as conditioning substances.

Preference is given to use of cationic surfactants from the group of alkyl trimethyl ammonium chlorides preferably having 10 to 18 carbon atoms in the alkyl radica, dialkyl dimethyl ammonium chloride preferably having 10 to 18 carbon atoms in the alkyl radical, cetyl trimethyl ammonium chloride, stearyltrimethylammonium chloride, distearyldimethylammonium chloride, lauryldimethylammonium chloride, lauryldimethylbenzylammonium chloride, tricetylmethylammonium chloride, Quaternium-27, Quaternium-83, N-methyl-N (2-hydroxyethyl)-N, N-(ditallow) ethyl) ammonium methosulfate, N-methyl-N (2-hydroxyethyl)-N, N-(distearyloxyethyl) ammonium methosulfate, N, N-dimethyl-N, N-distearoyloxyethyl ammonium chloride, N, N-di-(2-hydroxyethyl)-N, N-(fatty acid ester ethyl) ammonium chloride and mixtures thereof The cationic surfactant(s) is (are) preferably contained in the cosmetic agents used as contemplated herein in a total amount of from about 0.5 to about 50 wt. %, more preferably from about 1 to about 40 wt. %, even more preferably from about 1.5 to about 30 wt. %, particularly from about 2 to about 20 wt. % relative to the total weight of the cosmetic agent.

Suitable agents as contemplated herein are exemplified in that the agent additionally contains at least one anionic surfactant. Preferred anionic surfactants are fatty acids, alkyl sulfates, alkyl ether sulfates and ether carboxylic acids having from about 10 to about 20 C-atoms per alkyl group and up to 16 glycol ether groups per molecule.

Suitable agents as contemplated herein are exemplified in that the agent additionally contains at least one amphoteric surfactant. Preferred zwitterionic surfactants are betaine, n-alkyl-n, n-dimethyl ammonioum-glycinate, n-acyl-aminopropyl-n,n-dimethyl ammonium glycinate, and 2-alkyl-3-carboxymethyl-3-hydroxyethyl-imidazoline. A preferred zwitterionic surfactant is known by the INCI designation cocamidopropyl betaine.

Suitable agents as contemplated herein are exemplified in that the agent additionally contains at least one amphoteric surfactant. Preferred amphoteric surfactants are n-alkylglycines, n-alkylpropionic acids, n-alkylaminobutyric acids, n-alkyliminodipropionic acids, n-hydroxyethyl-n-alkylamidopropylglycines, n-alkyltaurines, n-alkyl sarcosines, 2-alkylaminopropionic acids and alkylaminoacetic acids. Particularly preferred amphoteric surfactants are N-cocosalkylaminopropionate, cocosacylaminoethylaminopropionate and $C_{12}$-$C_{18}$ acylsarcosin.

It has also proved advantageous for agents to contain other, non-ionogenic surfactants. Preferred non-ionic surfactants are alkyl polyglycosides as well as alkylene oxide binding agents to fatty alcohols and fatty acids with from about 2 to about 30 moles of ethylene oxide per mole of fatty alcohol or fatty acid. Preparations with outstanding properties are also obtained if they contain fatty acid esters of ethoxylated glycerol as nonionic surfactants.

The non-ionic, zwitterionic or amphoteric surfactants are used in proportions from about 0.1 to about 45 wt. %, preferably from about 1 to about 30 wt. % and more preferably from about 1 to about 15 wt. %, relative on the total quantity of the ready-to-use agent.

The agents as contemplated herein can contain at least one cationic thickener. There are essentially no limitations with respect to these thickening agents. Organic and purely inorganic thickening agents can be used.

Suitable thickening agents are anionic, synthetic polymers, cationic, synthetic polymers, naturally occurring thickening agents, such as nonionic guargium, scleroglucan, or xanthangium, gum arabic, ghatti gum, karaya gum, tragacanth gum, carrageenan gum, agar-agar, locust bean flour, pectins, alginates, starch fractions and derivatives such as amylose, amylopectin and dextrins, and cellulose derivatives, such as, for example, methyl cellulose, carboxyalkyl celluloses and hydroxyalkyl celluloses, non-ionic, fully synthetic polymers, such as polyvinyl alcohol or polyvinylpyrrolidinone; and inorganic thickening agents, in particular phyllosilicates such as, for example, bentonite, particularly smectites such as montmorillonite or hectorite.

It is also beneficial if the coloring agents, especially if they also contain hydrogen peroxide, contain at least one stabilizer or chelating agent. Particularly preferred stabilizers are phenacetin, alkali benzoates (sodium benzoate) and salicylic acid. Furthermore, all complexing agents of the prior art can be used. Preferred complexing agents as contemplated herein are nitrogen-containing polycarboxylic acids, in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP) or the sodium salts thereof.

he agents as contemplated herein can also contain other active ingredients, excipients and admixtures, such as non-ionic polymers, such as vinylpyrrolidinon/vinylacrylat-co-polymers, polyvinylpyrrolidinon, vinylpyrrolidinon/vinylacetat-copolymers, polyethylenglycols and polysiloxanes; additional silicones such as volatile or non-volatile, straight-chained, branched or cyclical, cross-linked or non-cross-linked polyalkylsiloxanes (such as dimethicones or cyclomethicones), polyarylsiloxanes and/or polyalkylarylsiloxanes, more particularly polysiloxanes with organofunctional groups such as substituted or unsubstituted amines (amodimethicones), carboxyl-, alkoxy- and/or hydroxyl groups (dimethiconcopolyols), line are polysiloxan(A)-polyoxyalkylen(B)-block copolymers, grafted silicon polymers; cationic polymers such as quaternized cellulose ether, polysiloxanes with quaternary groups, dimethyldiallylammoniumchlorid-polymers, acrylamid-dimethyldiallyl-ammonium chloride copolymers, with diethylsulfate quaternated dimethylamino-ethylmethacrylat-vinylpyrrolidinon-copolymers, vinylpyrrolidinon-imidazolinium-methochlorid-copolymers and quaternated polyvinyl alcohol; zwitterionic and amphoteric polymers; anionic polymers such as polyacryl acids or cross-linked polyacryl acids; structurants, such as glucose, malic acid and lactic acid, hair-conditioning compounds such as phospholipides, for example lecithin and cephalines; perfume oils, dimethylisosorbid and cyclodextrine; fiber structure-improving agents, more particularly mono-, di- and oligosaccharides, such as glucose, galactose, fructose, fruit sugar and lactose; dyes for coloring the preparations; anti-dandruff active ingredients such as piroctone olamine, zinc omadine and climbazol; amino acids and oligopeptides; protein hydrolysates on an animal and/or plant basis, as well as in the form of their fatty acid condensation products or, where applicable, anionically or cationically modified derivatives; plant oils; light stabilizers and UV blockers; active ingredients such as panthenol, pantothenic acid, pantolacton, allantoin, pyrrolidinoncarbonic acids and the salts thereof, as well as bisabolol; polyphenols, more particularlyhydroxy cinnamic acids, 6,7-dihydroxycumarines, hydroxybenzoic acids, catechins, tannins, flavanons, anthocyanidines, flavanons, flavons and flavonols; ceramides or pseudoceramides; vitamins, provitamins and vitamin precursors; plant extracts; fats and waxes such as fatty alcohols, beeswax, montan wax and paraffins; source and penetration substances such as glycerin, propylenglycolmonoethylether, carbonate, hydrogen carbonate, guanidine, urea, as well as primary, secondary and tertiary phosphates; opacifiers such as latex, styrene/PVP and styrene/acrylamide copolymers; pearl shine concentrates such as ethylenglycolmono- and -distearate as well as PEG-3-distearate; pigments as well as propellants such as propane-butane-mixtures, $N_2O$, dimethylether, $CO_2$ and air.

The person skilled in the art will select these other substances in accordance with the desired properties of the agent. With regard to further optional components and the amounts of these components used, reference is expressly made to the relevant handbooks known to the person skilled in the art. In the agents as contemplated herein, each of the active ingredients, excipients are preferably used in quantities from about 0.0001 to about 25 wt. %, particularly from about 0.0005 to about 15 wt. %, relative to the total weight of agent (A) and/or the oxidant preparation (B).

The kit or kits described above can be used in a method for oxidative dyeing and/or lightening of the hair. Particular preference is given to a method comprising the following steps:

A further subject of the present disclosure is a method for oxidative dyeing and/or lightening of hair comprising the following steps (1) application of preparation (A) on the hair, where preparation (A) is an agent containing at least one compound of formula (I), as disclosed in the description of the first subject of the present disclosure, (2) application of preparation (B) on the hair, where preparation (B) is an oxidant preparation containing at least one oxidant from the group of hydrogen peroxide, ammonium peroxodisulfate, potassium peroxodisulfate and sodium peroxodisulfate, (3) washing the hair.

The steps of the method can be carried out in different sequences.

Particular preference is given to a method exemplified in that the steps are carried out in the following sequence: step (1) followed by step (2) followed by step (3).

An additional preferred method is exemplified in that the steps are carried out in the following sequence: step (2) followed by step (1) followed by step (3).

Finally, another particularly preferred method is exemplified in that preparation (A) and preparation (B) are mixed with each other before application on the hair. If preparation (A) and preparataion (B) are mixed with each other before application on the hair, steps (1) and (2) are performed at the same time.

With respect to other preferred embodiments of the kit and process as contemplated herein, the statements made regarding the agents as contemplated herein apply mutatis mutandis.

EXAMPLES

1. Formulations

The following formulations were created (all data in wt. %)

1.1. Pre-Treatment Agent (VM)

| | VM1 | VM2 | VM3 |
|---|---|---|---|
| Citric acid (anhydrous) | | | 0.5 |
| Sodium lauryl ether sulfate (25% hydrous solution) | 50.0 | 50.0 | 50.0 |
| Disodium dicocoatepodicate | 7.0 | 7.0 | 7.0 |
| Salicylic acid | 0.2 | 0.2 | 0.2 |
| Sodium benzoate | 0.5 | 0.5 | 0.5 |
| Euperlan PK 300 AM (approx. 60-64% solids; INCI: glycol distearate, glycerine, laureth-4, cocamidopropyl betaine (cognis)) | 2.0 | 2.0 | 2.0 |
| Cetiol HE (coconut glyceride with approx. 7.3 EO units (INCI: PEG-7 glyceryl cocoate) (cognis)) | 1.0 | 1.0 | 1.0 |
| Oligopeptide# | 0.01 | 0.1 | 1.0 |
| Polyquaternium-10 | 0.5 | 0.5 | 0.5 |
| PEG-40 Hydrogenated Castor Oil | 1.0 | 1.0 | 1.0 |
| Sodium chloride | 0.5 | 0.5 | 0.5 |
| Water | ad 100 | ad 100 | ad 100 |

Oligopeptide mixture of formula (I), where R1 = formula (II), M1 = formula (III), x = 1-10 and y = 1-10, M2 = hydrogen, average molecular weight from about 400-about 800 Dalton

|  | VM4 | VM5 | VM6 |
|---|---|---|---|
| Citric acid (anhydrous) | 0.5 | 0.5 | 0.5 |
| Sodium lauryl ether sulfate (25% hydrous solution) | 50.0 | 50.0 | 50.0 |
| Disodium dicocoatepodicate | 7.0 | 7.0 | 7.0 |
| Salicylic acid | 0.2 | 0.2 | 0.2 |
| Sodium benzoate | 0.5 | 0.5 | 0.5 |
| Euperlan PK 300 AM (approx. 60-64% solids; INCI: glycol distearate, glycerine, laureth-4, cocamidopropyl betaine (cognis)) | 2.0 | 2.0 | 2.0 |
| Cetiol HE (coconut glyceride with approx. 7.3 EO units (INCI: PEG-7 glyceryl cocoate) (cognis)) | 1.0 | 1.0 | 1.0 |
| 2-amino-3-(sulfosulfanyl)propanoic acid | 0.01 | 0.1 | 1.0 |
| Polyquaternium-10 | 0.5 | 0.5 | 0.5 |
| PEG-40 Hydrogenated Castor Oil | 1.0 | 1.0 | 1.0 |
| Sodium chloride | 0.5 | 0.5 | 0.5 |
| Water | ad 100 | ad 100 | ad 100 |

1.2. Bleaching Powder (BP)

|  | BP1 | BP2 | BP3 | BP4 |
|---|---|---|---|---|
| Sodium metasilicate (anhydrous) | 11.8 | 11.8 | 11.8 | 11.8 |
| Sodium silicate | 23.8 | 23.8 | 23.8 | 23.8 |
| Magnesium carbonate | 22.5 | 22.5 | 22.5 | 22.5 |
| Sodium hexametaphosphate | 0.2 | 0.2 | 0.2 | 0.2 |
| Acrylates Copolymer (Rohagit s hv) (methyl methacrylate, methacrylic acid copolymer) | 2.0 | 2.0 | 2.0 | 2.0 |
| EDTA (disodium salt) | 0.2 | 0.2 | 0.2 | 0.2 |
| Oligopeptide[#] | — | 0.01 | 0.1 | 1.0 |
| Sodium persulfate | 14.5 | 14.5 | 14.5 | 14.5 |
| Ammonium persulfate | 10.0 | 10.0 | 10.0 | 10.0 |
| Paraffinum liquidum | ad 100 | ad 100 | ad 100 | ad 100 |

[#]Oligopeptide mixture of formula (I), where R1 = formula (II), M1 = formula (III), x = 1-10 and y = 1-10, average molecular weight 400-800 Dalton

|  | BP5 | BP6 | BP7 | BP8 |
|---|---|---|---|---|
| Sodium metasilicate (anhydrous) | 11.8 | 11.8 | 11.8 | 11.8 |
| Sodium silicate | 23.8 | 23.8 | 23.8 | 23.8 |
| Magnesium carbonate | 22.5 | 22.5 | 22.5 | 22.5 |
| Sodium hexametaphosphate | 0.2 | 0.2 | 0.2 | 0.2 |
| Acrylates Copolymer (Rohagit s hv) (methyl methacrylate, methacrylic acid copolymer) | 2.0 | 2.0 | 2.0 | 2.0 |
| EDTA (disodium salt) | 0.2 | 0.2 | 0.2 | 0.2 |
| 2-amino-3-(sulfosulfanyl)propanoic acid | — | 0.01 | 0.1 | 1.0 |
| Sodium persulfate | 10.5 | 10.5 | 10.5 | 10.5 |
| Potassium persulfate | 4.5 | 4.5 | 4.5 | 4.5 |
| Ammonium persulfate | 10.0 | 10.0 | 10.0 | 10.0 |
| Paraffinum liquidum | ad 100 | ad 100 | ad 100 | ad 100 |

1.3. Hydrogen Peroxide Preparation (OX)

|  | OX1 | OX2 | OX3 | OX4 |
|---|---|---|---|---|
| Hydrogen peroxide | 12.0 | 12.0 | 12.0 | 12.0 |
| Ammonia | 0.6 | 0.6 | 0.6 | 0.6 |
| Dipicolinic acid | 0.1 | 0.1 | 0.1 | 0.1 |
| Disodium pyrophosphate | 0.05 | 0.05 | 0.05 | 0.05 |
| 1-Hydroxyethane-1,1-diphosphonic acid (60% hydrous solution) | 1.5 | 1.5 | 1.5 | 1.5 |
| Sodium lauryl ether sulfate (25% hydrous solution) | 2.0 | 2.0 | 2.0 | 2.0 |

|  | OX1 | OX2 | OX3 | OX4 |
|---|---|---|---|---|
| Oligopeptide[#] | — | 0.01 | 0.1 | 1.0 |
| Aculyn 33 (acrylates copolymer) | 12.0 | 12.0 | 12.0 | 12.0 |
| Hydrogen peroxide | ad 100 | ad 100 | ad 100 | ad 100 |

[#]Oligopeptide mixture of formula (I), where R1 = formula (II), M1 = formula (III), x = 1-10 and y = 1-10, average molecular weight 400-800 Dalton

|  | OX5 | OX6 | OX7 | OX8 |
|---|---|---|---|---|
| Hydrogen peroxide | 18.0 | 18.0 | 18.0 | 18.0 |
| Ammonia | 0.6 | 0.6 | 0.6 | 0.6 |
| Dipicolinic acid | 0.1 | 0.1 | 0.1 | 0.1 |
| Disodium pyrophosphate | 0.05 | 0.05 | 0.05 | 0.05 |
| 1-Hydroxyethane-1,1-diphosphonic acid (60% hydrous solution) | 1.5 | 1.5 | 1.5 | 1.5 |
| Sodium lauryl ether sulfate (25% hydrous solution) | 2.0 | 2.0 | 2.0 | 2.0 |
| 2-amino-3-(sulfosulfanyl)propanoic acid | — | 0.01 | 0.1 | 1.0 |
| Aculyn 33 (acrylates copolymer) | 12.0 | 12.0 | 12.0 | 12.0 |
| Hydrogen peroxide | ad 100 | ad 100 | ad 100 | ad 100 |

1.4. Post-Treatment Agent (NM)

|  | NM1 | NM2 | NM3 |
|---|---|---|---|
| Paraffinum liquidum | 1.0 | 1.0 | 1.0 |
| Dehyquart F75 (INCI name: Distearoylethyl Hydroxyethylmonium Methosulfate, Cetearyl Alcohol) | 2.0 | 2.0 | 2.0 |
| Oligopeptide[#] | 0.01 | 0.1 | 1.0 |
| Quaternium-87 | 1.5 | 1.5 | 1.5 |
| Cetearyl alcohol | 3.5 | 3.5 | 3.5 |
| Propylparaben | 0.15 | 0.15 | 0.15 |
| Cetyl paltimate | 0.7 | 0.7 | 0.7 |
| Stearamidopropyl dimethylamine | 1.0 | 1.0 | 1.0 |
| Trimethylhexadecylammonium chloride | 0.6 | 0.6 | 0.6 |
| Citric acid | 0.5 | 0.5 | 0.5 |
| Methylparaben | 0.15 | 0.15 | 0.15 |
| Water | ad 100 | ad 100 | ad 100 |

[#]Oligopeptide mixture of formula (I), where R1 = formula (II), M1 = formula (III), x = 1-10 and y = 1-10, average molecular weight 400-800 Dalton Post-Treatment Agent (NM)

|  | NM4 | NM5 | NM6 |
|---|---|---|---|
| Paraffinum liquidum | 1.0 | 1.0 | 1.0 |
| Dehyquart F75 (INCI name: Distearoylethyl Hydroxyethylmonium Methosulfate, Cetearyl Alcohol) | 2.0 | 2.0 | 2.0 |
| 2-amino-3-(sulfosulfanyl)propanoic acid | 0.01 | 0.1 | 1.0 |
| Quaternium-87 | 1.5 | 1.5 | 1.5 |
| Cetearyl alcohol | 3.5 | 3.5 | 3.5 |
| Propylparaben | 0.15 | 0.15 | 0.15 |
| Cetyl paltimate | 0.7 | 0.7 | 0.7 |
| Stearamidopropyl dimethylamine | 1.0 | 1.0 | 1.0 |
| Trimethylhexadecylammonium chloride | 0.6 | 0.6 | 0.6 |
| Citric acid | 0.5 | 0.5 | 0.5 |
| Methylparaben | 0.15 | 0.15 | 0.15 |
| Water | ad 100 | ad 100 | ad 100 |

2. Bleaching

Hair strands (Kerling dark brown) were treated according to the following method.

The pre-treatment agents (VM) were applied to hair strands (4 g of pre-treatment agent per g of hair strand) and left there for 5 minutes at room temperature. Then the hair strands were washed with water and dried in a hand-warm air flow.

The bleaching powder (BP) was mixed with the hydrogen peroxide preparation (OX) in a ratio of 1:2 (1 part BP to 2 parts OX). This ready-to-use bleaching agent was applied to the hair strands and left there for 30 minutes at room temperature. Then the hair strands were washed with water and dried in a hand-warm air flow.

The post-treatment agents (NM) were applied to hair strands (4 g of pre-treatment agent per g of hair strand) and left there for 5 minutes at room temperature. Then the hair strands were washed with water and dried in a hand-warm air flow.

Procedure

|  | 1. | 2 | 3 | 4 | 5 |
|---|---|---|---|---|---|
| Pre-treatment | — | — | — | — | — |
| Bleaching | BP1 + OX2 | BP1 + OX3 | BP1 + OX4 | BP2 + OX1 | BP3 + OX1 |
| Post-treatment | — | — | — | — | — |

|  | 6 | 7 | 8 | 9 | 10 |
|---|---|---|---|---|---|
| Pre-treatment | — | — | — | — | — |
| Bleaching | BP4 + OX1 | BP2 + OX2 | BP2 + OX4 | BP3 + OX3 | BP4 + OX4 |
| Post-treatment | — | — | — | — | — |

|  | 11 | 12 | 13 | 14 | 15 |
|---|---|---|---|---|---|
| Pre-treatment | — | — | — | — | — |
| Bleaching | BP5 + OX6 | BP5 + OX7 | BP5 + OX8 | BP6 + OX5 | BP7 + OX5 |
| Post-treatment | — | — | — | — | — |

|  | 16 | 17 | 18 | 19 | 20 |
|---|---|---|---|---|---|
| Pre-treatment | — | — | — | — | — |
| Bleaching | BP8 + OX5 | BP6 + OX6 | BP6 + OX8 | BP7 + OX7 | BP8 + OX8 |
| Post-treatment | — | — | — | — | — |

|  | 21 | 22 | 23 | 24 | 25 |
|---|---|---|---|---|---|
| Pre-treatment | VM1 | VM2 | VM3 | VM2 | VM3 |
| Bleaching | BP1 + OX2 | BP1 + OX3 | BP1 + OX4 | BP2 + OX1 | BP3 + OX1 |
| Post-treatment | — | — | — | — | — |

|  | 26 | 27 | 28 | 29 | 30 |
|---|---|---|---|---|---|
| Pre-treatment | — | — | — | — | — |
| Bleaching | BP4 + OX1 | BP2 + OX2 | BP2 + OX4 | BP3 + OX3 | BP4 + OX4 |
| Post-treatment | NM1 | NM2 | NM3 | NM2 | NM3 |

|  | 31 | 32 | 33 | 34 | 35 |
|---|---|---|---|---|---|
| Pre-treatment | VM4 | VM5 | VM6 | VM5 | VM6 |
| Bleaching | BP5 + OX6 | BP5 + OX7 | BP5 + OX8 | BP6 + OX5 | BP7 + OX5 |
| Post-treatment | — | — | — | — | — |

|  | 36 | 37 | 38 | 39 | 40 |
|---|---|---|---|---|---|
| Pre-treatment | — | — | — | — | — |
| Bleaching | BP8 + OX5 | BP6 + OX6 | BP6 + OX8 | BP7 + OX7 | BP8 + OX8 |
| Post-treatment | NM4 | NM5 | NM6 | NM5 | NM6 |

|  | 21 | 22 | 23 | 24 | 25 |
|---|---|---|---|---|---|
| Pre-treatment | VM1 | VM2 | VM3 | VM2 | VM3 |
| Bleaching | BP1 + OX3 | BP1 + OX4 | BP2 + OX1 | BP4 + OX1 | BP4 + OX4 |
| Post-treatment | NM1 | NM2 | NM3 | NM2 | NM3 |

|  | 31 | 32 | 33 | 34 | 35 |
|---|---|---|---|---|---|
| Pre-treatment | VM4 | VM5 | VM6 | VM5 | VM6 |
| Bleaching | BP5 + OX6 | BP5 + OX8 | BP6 + OX5 | BP6 + OX8 | BP7 + OX7 |
| Post-treatment | NM4 | NM5 | NM6 | NM5 | NM6 |

3. Care Drops (PT)

1.1. Pre-Treatment Agent (VM)

|  | PT1 | PT2 | PT3 |
|---|---|---|---|
| Oligopeptide[#] | 0.01 | 1.0 | 10.0 |
| Water | ad 100 | ad 100 | ad 100 |

[#]Oligopeptide mixture of formula (I), where R1 = formula (II), M1 = formula (III), x = 1-10 and y = 1-10, M2 = hydrogen, average molecular weight 400-800 Dalton

|  | PT4 | PT5 | PT6 |
|---|---|---|---|
| 2-amino-3-(sulfosulfanyl)propanoic acid | 0.01 | 1.0 | 10.0 |
| Water | ad 100 | ad 100 | ad 100 |

The bleaching powder (BP) was mixed with the hydrogen peroxide preparation (OX) and the care drops (PT) in a ratio of 1:2:0.5 (w parts BP to 4 parts OX to one part PT).

This ready-to-use bleaching agent was applied to the hair strands and left there for 30 minutes at room temperature. Then the hair strands were washed with water and dried in a hand-warm air flow.

Procedure

|  | 36 | 37 | 38 |
|---|---|---|---|
| Pre-treatment | — | — | — |
| Bleaching | BP1 + OX1 + PT1 | BP1 + OX1 + PT2 | BP1 + OX1 + PT3 |
| Post-treatment | — | — | — |

|  | 39 | 40 | 41 |
|---|---|---|---|
| Pre-treatment | — | — | — |
| Bleaching | BP5 + OX5 + PT4 | BP5 + OX5 + PT5 | BP5 + OX5 + PT6 |
| Post-treatment | — | — | — |

The invention claimed is:

1. A hair treatment agent, comprising in a cosmetic carrier
(a) at least one compound of the general formula (I)

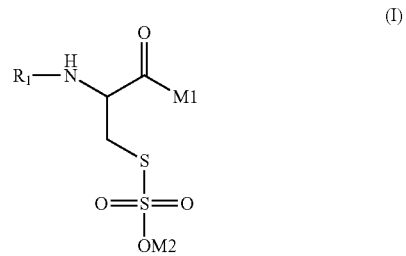

wherein

R₁ denotes a structural element of formula (II)

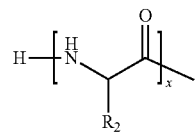
(II)

wherein x denotes an integer from 1 to 100, the radical R₂ in each of the structural elements of formula (II) can be selected independently of the preceding structural element of formula (II), R₂ denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, and M1 denotes the grouping —OM2 or a structural element of formula (III)

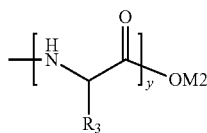
(III)

wherein y denotes an integer from 1 to 100, the radical R₃ in each of the structural elements of formula (III) can be selected independently of the preceding structural element of formula (III), R₃ denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, and M2 denotes a hydrogen atom, an equivalent of one or more cations or an ammonia ion (NH₄)⁺.

2. The hair treatment agent according to claim 1, comprising at least one compound of formula (I), wherein M1 denotes a —OM2 grouping.

3. A hair treatment agent, comprising in a cosmetic carrier (a) at least one compound of the general formula (I)

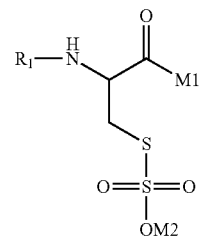
(I)

wherein

R₁ denotes a hydrogen atom or a structural element of formula (II)

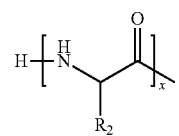
(II)

wherein x denotes an integer from 1 to 100, the radical R₂ in each of the structural elements of formula (II) can be selected independently of the preceding structural element of formula (II), R₂ denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimi dami dopropyl group, a 2-carb oxyethyl group, a carboxymethyl group, a 2-carb amoyl ethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, and M1 denotes a structural element of formula (III)

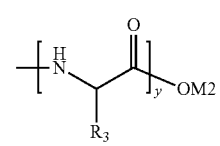
(III)

wherein y denotes an integer from 1 to 100, the radical R₃ in each of the structural elements of formula (III) can be selected independently of the preceding structural element of formula R₃ denotes a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-amino butyl group, a 3-carbimi dami dopropyl group, a 2-carb oxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, and M2 denotes a hydrogen atom, an equivalent of one or more cations or an ammonia ion $(NH_4)^+$.

4. The hair treatment agent according to claim 1 comprising at least one compound of formula (I), wherein M1 denotes a structural element of formula (III), x denotes an integer from 1 to 10, and y denotes an integer from 1 to 10.

5. The hair treatment agent according to claim 1 comprising at least one compound of formula (I), wherein the radical $R_2$ denotes a (sulfosulfanyl)methyl group in at least one structural element of formula (II).

6. The hair treatment agent according to claim 3 comprising at least one compound of formula (I), wherein the radical $R_3$ denotes a (sulfosulfanyl)methyl group in at least one structural element of formula (III).

7. The hair treatment agent according to claim 1 comprising at least one compound of formula (I), wherein x denotes an integer from at least 3, and the radical $R_2$ denotes a 2-carboxyethyl group in at least 3 structural elements of formula (II).

8. The hair treatment agent according to claim 3 comprising least one compound of formula (I), wherein y denotes an integer from at least 3, and the radical $R_3$ denotes a 2-carboxyethyl group in at least 3 structural elements of formula (III).

9. The hair treatment agent according to claim 1 comprising one or multiple compounds of formula (I) in a total amount of from about 0.0001 to about 10.0 wt. %.

10. The hair treatment agent according to claim 1 further comprising (b) at least one peroxide compound as an oxidant selected from the group of hydrogen peroxide, ammonium peroxodisulfate, potassium peroxodisulfate, sodium peroxodisulfate.

11. The hair treatment agent according to claim 1 further comprising (b) hydrogen peroxide as an oxidant.

12. The hair treatment agent according to claim 10 comprising (a) the compound(s) of formula (I) and (b) the oxidant in a weight ratio (a)/(b) of 1:20.

13. A kit for oxidative dyeing or lightening of hair comprising at least two separately packaged preparations (A) and (B), wherein preparation (A) is an agent according to claim 1, and preparation (B) is an oxidant preparation comprising at least one oxidant selected from the group of ammonia peroxodisulfate, potassium peroxodisulfate, sodium peroxodisulfate.

14. A kit for oxidative dyeing or lightening of hair comprising at least two separately packaged preparations (A) and (B), wherein preparation (A) is an agent according to claim 1 and preparation (B) is an oxidant preparation comprising hydrogen peroxide.

15. A method for oxidative dyeing or lightening of hair, comprising the following steps (1) application of preparation (A) on the hair, where preparation (A) is a hair treatment agent, comprising, in a cosmetic carrier:

at least one compound of the general formula (I)

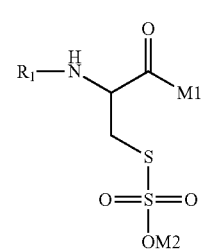

(I)

wherein $R_1$ denotes a hydrogen atom or a structural element of formula (II)

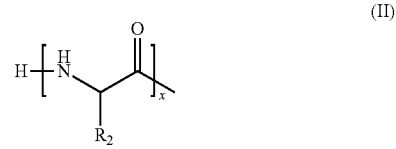

(II)

wherein x denotes an integer from 1 to 100, the radical $R_2$ in each of the structural elements of formula (II) can be selected independently of the preceding structural element of formula (II), $R_2$ denotes a hydrogen atom, a methyl group, an isopropyl group, a 2-methylpropyl group, a 1-methylpropyl group, a benzyl group, a 4-hydroxybenzyl group, a hydroxymethyl group, 1-hy droxy ethyl group, a 4-amino butyl group, a 3-carb i mi dami dopropyl group, a 2-carb oxy ethyl group, a carboxymethyl group, a 2-carbamoylethyl group, a carbamoylmethyl group, a sulfanylmethyl group, a 2-(methylsulfanyl) ethyl group, a 1H-imidazol-4-ylmethyl group, a 1H-indol-3-ylmethyl group or a (sulfosulfanyl)methyl group, and M1 denotes the grouping —OM2 or a structural element of formula (III)

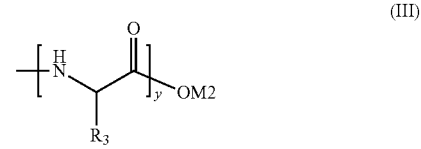

(III)

wherein y denotes an integer from 1 to 100, the radical $R_3$ in each of the structural elements of formula (III) can be selected independently of the preceding structural element of formula (III), $R_3$ denotes a hydrogen atom, a methyl group, an isopropyl group, a 2-methylpropyl group, a 1-methylpropyl group, a benzyl group, a 4-hydroxybenzyl group, a hydroxymethyl group, 1 -hy droxy ethyl group, a 4-amino butyl group, a 3-carb i mi dami dopropyl group, a 2-carb oxy ethyl group, a carboxymethyl group, a 2-carbamoylethyl group, a carbamoylmethyl group, a sulfanylmethyl group, a 2-(methylsulfanyl) ethyl group, a 1H-imidazol-4-ylmethyl group, a 1H-indol-3-ylmethyl group or a (sulfosulfanyl)methyl group, and M2 denotes a hydrogen atom, an equivalent of one or more cations or an ammonia ion $(NH_4)^+$;

(2) application of preparation (B) on the hair, where preparation (B) is an oxidant preparation comprising at least one oxidant selected from the group of hydrogen peroxide, ammonium peroxodisulfate, potassium peroxodisulfate and sodium peroxodisulfate, and wherein preparation (A) and preparation (B) may optional be combined prior to application to the hair; and (3) washing the hair.

16. The method according to claim 15 wherein the steps are carried out in the following sequence: step (1) followed by step (2) followed by step (3).

17. The method according to claim 15 wherein the steps are carried out in the following sequence: step (2) followed by step (1) followed by step (3).

18. The method according to claim 15 wherein preparation (A) and preparation (B) are mixed with each other before application on the hair, and wherein step (3) follows the application of mixed preparation (A) and preparation (B) on the hair.

* * * * *